(12) United States Patent
Wu et al.

(10) Patent No.: US 8,530,487 B1
(45) Date of Patent: Sep. 10, 2013

(54) COMPOUNDS USEFUL FOR TREATING DISORDERS RELATED TO TRPA1

(75) Inventors: Xinyuan Wu, Newton, MA (US); Spencer David Kimball, East Windsor, NJ (US); Ping Chen, Franklin Park, NJ (US); Ding Zhou, Shanghai (CN); Shaoping Peng, Shanghai (CN)

(73) Assignee: Hydra Biosciences, Inc., Cambridge, MA (US)

( * ) Notice: Subject to any disclaimer, the term of this patent is extended or adjusted under 35 U.S.C. 154(b) by 471 days.

(21) Appl. No.: 12/696,618

(22) Filed: Jan. 29, 2010

Related U.S. Application Data

(60) Provisional application No. 61/148,296, filed on Jan. 29, 2009.

(51) Int. Cl.
| | | |
|---|---|---|
| A01N 43/54 | (2006.01) | |
| A61K 31/505 | (2006.01) | |
| C07D 239/00 | (2006.01) | |
| C07D 471/00 | (2006.01) | |

(52) U.S. Cl.
USPC .......................................... 514/267; 544/250

(58) Field of Classification Search
USPC ........................................ 514/267; 544/250
See application file for complete search history.

(56) References Cited

U.S. PATENT DOCUMENTS

| 2007/0073505 A1 | 3/2007 | Bliss et al. |
| 2011/0124666 A1 | 5/2011 | Gijsen et al. |

FOREIGN PATENT DOCUMENTS

| EP | 0489991 | 12/1990 |
| WO | 2007073505 | 6/2007 |
| WO | 2007098252 | 8/2007 |
| WO | 2009147079 | 12/2009 |

OTHER PUBLICATIONS

Kondo, et al., Transient Receptor Potential A1 Mediates Gastric Distention-induced Visceral Pain in Rats, Gut 58, 1342-52 (2009).*
Kappe, et al., 100 Years of the Biginelli Dihydropyrimidine Synthesis, Tetrahedron, vol. 49, 336, 6937-6963 (1993).*
Bautista et al., "Pungent products from garlic activate the sensory ion channel TRPA1." 102(34):12248-12252 (2005).
Berge et al. "Pharmaceutical Salts", J. Pharm. Sci. 66:1-19. (1977).
Bessec, et al., Sensory Detection and Responses to Toxic Gases, Proc. Am. Thorac. Soc., vol. 7, pp. 269-277 (2010).
Buzzi et al, "The antimigraine drug, sumatriptan (GR43175), selectively blocks neurogenic plasma extravasation from blood vessels in dura mater." Br J Pharmacol; 99:202-206 (1990).
Dotto, "Signal transduction pathways controlling the switch between keratinocyte growth and differentiation." Crit Rev Oral Biol Med 10:442-457 1999.
Hauser et al. "PAF-mediated Ca2+ influx in human neutrophils occurs via store-operated mechanisms." J. Leukocyte Biology 69 (1):63-68 (2001).
Hinman et al., "TRP channel activation by reversible covalent modification" PNAS 103 (51): 19564-19568 2006.
Ito et al. "Internal Ca2+ mobilization is altered in fibroblasts from patients with Alzheimer disease." Proc. Natl. Acad. Sci. U.S.A. 91:534-538 (1994).
Jaquemar et al. "An ankyrin-like protein with transmembrane domains is specifically lost after oncogenic transformation of human fibroblasts." J Biol Chem 274(11): 7325-33 (1999).
Kimball et al., "Acute colitis induction by oil of mustard results in later development of an IBS-like accelerated upper GI transit in mice." Am J Physiol Gastrointest Liver Physiol, 288(6):G1266-73 (2005).
Kuhnz et al., "Predicting the oral bioavailability of 19-nortestosterone progestins in vivo from their metabolic stability in human liver microsomal preparations in vitro." Drug Metabolism and Disposition vol. 26, 1120-27 (1998).
Leissring et al. "Alzheimer's presenilin-1 mutation potentiates inositol 1,4,5-trisphosphate-mediated calcium signaling in Xenopus oocytes." J. Neurochemistry, 72:1061-1068 (1999).
Leissring et al. "Calsenilin reverses presenilin-mediated enhancement of calcium signaling." Proc. Natl. Acad. Sci. U.S.A. 97(15):8590-8593 (2000).
Leissring et al. "Capacitative calcium entry deficits and elevated luminal calcium content in mutant presenilin-1 knockin mice." J. Cell Biol. 149(4):793-797 (2000).
Leissring et al. "Presenilin-2 mutations modulate amplitude and kinetics of inositol 1, 4,5-trisphosphate-mediated calcium signals." J. Biol. Chem. 274(46):32535-32538 (1999).
Macpherson, et al. "Noxious compounds activate TRPA 1 ion channels through covalent modification of cysteines", Nature, 1-5 2007.
McGaraughty et al. "Effects of A-317491, a novel and selective P2X3/P2X2/3 receptor antagonist, on neuropathic, inflammatory and chemogenic nociception following intrathecal and intraplantar administration" Br J Pharmacol 140: 1381-1388 (2003).
McLeod et al. "Nociceptin inhibits cough in the guinea-pig by activation of ORL(1) receptors" (2001) Br J Pharmacol 132: 1175-1178.
Nagata et al. "Nociceptor and hair cell transducer properties of TRPA1, a channel for pain and hearing" J. Neurosci 25 (16) 4052-61 (2005).
Riazimand "A rat model for studying effects of sacral neuromodulation on the contractile activity of a chronically inflamed bladder." BJU 94: 158-163 (2004).
Rouget et al. "Nociceptin inhibits airway microvascular leakage induced by HCI intra-oesophageal instillation." Br J Pharmacol 141: 1077-1083 (2004).
Tanaka et al., "Cough reflex induced by microinjection of citric acid into the larynx of guinea pigs: new coughing model." Journal Pharmacol Sci 93: 465-470 (2003).
Walker et al. "The VR1 antagonist capsazepine reverses mechanical hyperalgesia in models of inflammatory and neuropathic pain." Journal of Pharmacol Exp Ther 304: 56-62 (2003).
Yoo et al. "Presenilin-mediated modulation of capacitative calcium entry." Neuron, 27(3):561-572 (2000).
International Search Report from PCT/EP2009/056593 mailed on Jul. 23, 2009.
International Preliminary Report on Patentability from PCT/EP2009/056593 dated Dec. 6, 2010.
Kappe et al "100 Years of the Biginelli Dihydropyrimidine Synthesis" Tetrahedron 1993 vol. 49 pp. 6937-6963 Tetrahedron Report No. 336.

(Continued)

Primary Examiner — Erich A Leeser
(74) Attorney, Agent, or Firm — Lando & Anastasi LLP

(57) ABSTRACT

Compounds and compositions for treating disorders related to TRPA1 are described herein.

11 Claims, No Drawings

(56) References Cited

OTHER PUBLICATIONS

Ali et al "Synthesis and Reactions of 2,3-Didydro-5-Aryl-5H,6HTHIAZOLO[3,2b]-2,4-Diazafluorene-3,6,Diones of Potential Biological Activities" Phosphorous and Sulfur 1988 vol. 39 pp. 211-216.

Bautista et al "TRPA1 Mediates the Inflammatory Actions of Environmental Irritants and Proalgesic Agents" Cell 2006 vol. 124 pp. 1269-1282.

Levine et al "TRP Channels: Targets for the Relief of Pain" Biochimica Et Biophysica Acta 2007 vol. 1772 pp. 989-1003.

McMahon et al "Increasingly Irritable and Close to Tears: TRPA1 in Inflammatory Pain" Cell 2006 vol. 124 pp. 1122.

McNamara et al "TRPA1 Mediates Formalin-Induced Pain" PNAS 2007 vol. 104(33) pp. 13525-13530.

Shanmugam et al "Synthesis of Fused Dihydropyrimidones From Cyclic-1,3-Dicarbonyl Compounds: Modified Biginelli Synthesis of 1,2,3,4,5,6,7,8-Octahydroquinazolinediones and 3,4-Dihyrod-1-H-Indeno[1,2-D]Pyrimidine-2,5-Diones" Indian Journal of Chemistry 2004 vol. 43B, pp. 134-140.

Trevisani et al "4-Hydroxynonenal an Endogenous Aldehyde Causes Pain and Neurogenic Inflammation Through Activation of the Irritant Receptor TRPA1" PNAS 2007 vol. 104(33) pp. 13519-13524.

Zanderson et al "Synthesis and Properties of Some Derivatives of 2-Thionoindeno[1,2,-d]-Pyrimidine and Indeno[1,2-d]Thiazine" Chemistry of Heterocyclic Compounds ENG Trans 1988 vol. 24 pp. 936-941 Translated From Russian.

\* cited by examiner

COMPOUNDS USEFUL FOR TREATING DISORDERS RELATED TO TRPA1

PRIORITY CLAIM

This application claims priority to U.S. Ser. No. 61/148,296, filed Jan. 29, 2009, which is hereby incorporated by reference in its entirety.

BACKGROUND

The invention relates to compounds and compositions useful for treating disorders related to TRPA1.

A variety of ion channel proteins exist to mediate ion flux across cellular membranes. The proper expression and function of ion channel proteins is essential for the maintenance of cell function and intracellular communication. Numerous diseases are the result of misregulation of membrane potential or aberrant calcium handling. Given the central importance of ion channels in modulating membrane potential and ion flux in cells, identification of agents that can promote or inhibit particular ion channels are of great interest, both as research tools and as therapeutic agents.

SUMMARY OF THE INVENTION

The invention provides compounds, methods and compositions for treating or preventing conditions such as pain by modulating the activity of the TRPA1 channel. The compounds described herein can modulate the function of TRPA1 by inhibiting a TRPA1-mediated ion flux or by inhibiting the inward current, the outward current, or both currents mediated by TRPA1. The inhibition of a particular current is the ability to inhibit or reduce such current (e.g., inward and/or outward) in an in vitro or an in vivo assay. (See Jordt et al. (2004), Nature 427:260-265; Bautista et al., (2005) PNAS: 102(34):12248-12252).

In one aspect, the invention features a method of treating a TRPA1 mediated disorder in a subject. The method includes administering an effective amount of a compound of formula I, or a pharmaceutically acceptable salt thereof:

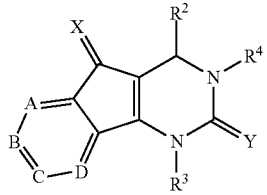

Formula I

Each of A, B, C, and D is $CR^1$ or N, provided that no more than 2 of A, B, C, and D are N; in addition, each of X and Y is, independently, N—R, O or S, where R is H, optionally substituted $C_{1-6}$ alkyl, OH, OR', CN, $NO_2$, or $SO_2R'$, where R' is H or $C_{1-6}$ alkyl; each $R^1$ is, independently, H, optionally substituted $C_{1-6}$ alkyl, optionally substituted $C_{2-6}$ alkenyl, optionally substituted $C_{2-6}$ alkynyl, optionally substituted heterocyclyl, hydroxyl, optionally substituted $C_{1-6}$ alkoxy, optionally substituted $C_{1-6}$ alkenyloxy, cyano, halo, acyl, amino, optionally substituted alkylamino, aminoalkyl, amido, acylamino, alkylurea, alkylcarbamoyl, carboxyl, optionally substituted alkylcarboxyl, thioyl, optionally substituted alkylthio, $SO_3H$, alkylsulfinyl, optionally substituted alkylsulfonyl, or nitro. $R^2$ is optionally substituted cycloalkyl, optionally substituted heterocyclyl, optionally substituted aryl or optionally substituted heteroaryl; each of $R^3$ and $R^4$ is, independently, H, optionally substituted $C_{1-6}$ alkyl, arylalkyl, heteroarylalkyl, alkoxyalkyl, $COR^{10}$, $CO_2R^{10}$, $CH_2CO_2R^{10}$, or $CONHR^{10}$, where $R^{10}$ is H or optionally substituted $C_{1-6}$ alkyl. In some embodiments, at least one of A, B, C, or D is N. For example, in some embodiments, D is N.

In another aspect, the invention features a method of treating pain in a subject. The method includes administering an effective amount of a compound of formula I, or a pharmaceutically acceptable salt thereof:

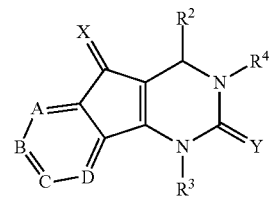

Formula I where the substituents are defined as above. In some embodiments, at least one of A, B, C, or D is N. For example, in some embodiments, D is N.

In another aspect, the invention features a compound having Formula III, or a pharmaceutically acceptable salt thereof:

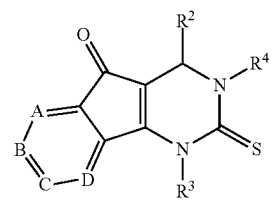

Formula III where each of A, B, C, and D is $CR^1$ or N, provided that no more than 2 of A, B, C, and D are N. In addition, each $R^1$ is, independently, H, optionally substituted $C_{1-6}$ alkyl, optionally substituted $C_{2-6}$ alkenyl, optionally substituted $C_{2-6}$ alkynyl, optionally substituted heterocyclyl, hydroxyl, optionally substituted $C_{1-6}$ alkoxy, $C_{1-6}$ alkenyloxy, cyano, halo, acyl, amino, optionally substituted alkylamino, aminoalkyl, amido, acylamino, alkylurea, alkylcarbamoyl, carboxyl, optionally substituted alkylcarboxyl, thioyl, optionally substituted alkylthio, $SO_3H$, optionally substituted alkylsulfinyl, optionally substituted alkylsulfonyl, or nitro; $R^2$ is optionally substituted cycloalkyl, optionally substituted heterocyclyl, optionally substituted aryl or optionally substituted heteroaryl; and each of $R^3$ and $R^4$ is, independently, H, optionally substituted $C_{1-6}$ alkyl, arylalkyl, heteroarylalkyl, alkoxyalkyl, $COR^{10}$, $CO_2R^{10}$, $CH_2CO_2R^{10}$, or $CONHR^{10}$, where $R^{10}$ is H or optionally substituted $C_{1-6}$ alkyl. However, when A, B, C, and D are all CH, and $R^3$ and $R^4$ are both H, then $R^2$ cannot be 3-nitrophenyl, naphthyl, 2-halophenyl, 3,4,5-trimethoxyphenyl, 2,3-dihydroxyphenyl, unsubstituted phenyl, pyridyl, 4-alkylphenyl, 4-alkoxyphenyl, 4-hydroxyphenyl, 4-halophenyl, 4-nitrophenyl, benzo-11,31-dioxole. In addition, when A, B, C, and D are all CH and $R^2$ is unsubstituted phenyl or 3,4,5-trimethoxyphenyl, then neither of $R^3$ and $R^4$ can be methyl.

In some embodiments, at least one of A, B, C, or D is N. For example, in some embodiments, D is N. In some embodiments, $R^2$ is optionally substituted phenyl, e.g., meta-substituted phenyl.

In another aspect, the invention features a compound of Formula V, or a pharmaceutically acceptable salt thereof:

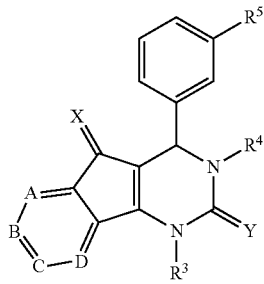

Formula V where each of A, B, C, and D is $CR^1$ or N, provided that no more than 2 of A, B, C, and D are N;
each of X and Y is, independently, N—R, O or S, where R is H, alkyl, OH, OR', CN, $NO_2$, or $SO_2R'$, where R' is H or $C_{1-6}$ alkyl; each $R^1$ is, independently, H, optionally substituted $C_{1-6}$ alkyl, optionally substituted $C_{2-6}$ alkenyl, optionally substituted $C_{2-6}$ alkynyl, optionally substituted heterocyclyl, hydroxyl, optionally substituted $C_{1-6}$ alkoxy, optionally substituted $C_{1-6}$ alkenyloxy, cyano, halo, acyl, amino, optionally substituted alkylamino, aminoalkyl, amido, acylamino, alkylurea, alkylcarbamoyl, carboxyl, optionally substituted alkylcarboxyl, thioyl, optionally substituted alkylthio, $SO_3H$, optionally substituted alkylsulfinyl, optionally substituted alkylsulfonyl, or nitro; each of $R^3$ and $R^4$ is, independently, H, optionally substituted $C_{1-6}$ alkyl, arylalkyl, heteroarylalkyl, alkoxyalkyl, $COR^{10}$, $CO_2R^{10}$, $CH_2CO_2R^{10}$, or $CONHR^{10}$, where $R^{10}$ is H or optionally substituted $C_{1-6}$ alkyl; $R^5$ is hydroxyl, optionally substituted $C_{1-6}$ alkoxy, optionally substituted $C_{1-6}$ alkenyloxy, alkyloxyalkoxy, cyano, acyl, amino, optionally substituted alkylamino, aminoalkyl, amido, acylamino, alkylurea, alkylcarbamoyl, carboxyl, optionally substituted alkylcarboxyl, thioyl, optionally substituted alkylthio, $SO_3H$, optionally substituted alkylsulfinyl, or optionally substituted alkylsulfonyl. In some embodiments, at least one of A, B, C, or D is N. For example, in some embodiments, D is N.

In another aspect, the invention features a compound having Formula VII, or a pharmaceutically acceptable salt thereof:

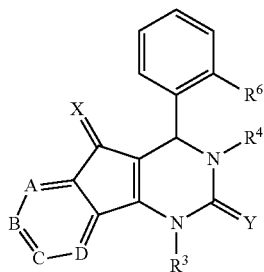

Formula VII where each of A, B, C, and D is $CR^1$ or N, provided that no more than 1 of A, B, C, and D is N;
each of X and Y is, independently, N—R, O or S, where R is H, alkyl, OH, OR', CN, $NO_2$, or $SO_2R'$, where R' is H or $C_{1-6}$ alkyl; each $R^1$ is, independently, H, optionally substituted $C_{1-6}$ alkyl, optionally substituted $C_{2-6}$ alkenyl, optionally substituted $C_{2-6}$ alkynyl, optionally substituted heterocyclyl, hydroxyl, optionally substituted $C_{1-6}$ alkoxy, optionally substituted $C_{1-6}$ alkenyloxy, cyano, halo, acyl, amino, optionally substituted alkylamino, aminoalkyl, amido, acylamino, alkylurea, alkylcarbamoyl, carboxyl, optionally substituted alkylcarboxyl, thioyl, optionally substituted alkylthio, $SO_3H$, optionally substituted alkylsulfinyl, optionally substituted alkylsulfonyl, or nitro; each of $R^3$ and $R^4$ is, independently, H, optionally substituted $C_{1-6}$ alkyl, arylalkyl, heteroarylalkyl, alkoxyalkyl, $COR^{10}$, $CO_2R^{10}$, $CH_2CO_2R^{10}$, or $CONHR^{10}$, where $R^{10}$ is H or optionally substituted $C_{1-6}$ alkyl; $R^6$ is hydroxyl, $C_{1-6}$ alkenyloxy, cyano, acyl, amino, optionally substituted alkylamino, aminoalkyl, amido, acylamino, alkylurea, alkylcarbamoyl, carboxyl, optionally substituted alkylcarboxyl, thioyl, optionally substituted alkylthio, $SO_3H$, optionally substituted alkylsulfinyl, or optionally substituted alkylsulfonyl. In some embodiments, at least one of A, B, C, or D is N. For example, in some embodiments, D is N.

In another aspect, the invention features a compound having Formula VIII, or a pharmaceutically acceptable salt thereof:

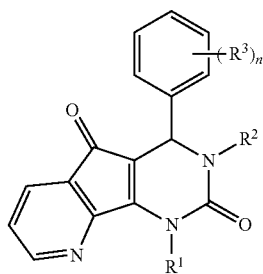

Formula VIII wherein each of R1 and $R^2$ is, independently, H, optionally substituted $C_{1-6}$ alkyl, arylalkyl, heteroarylalkyl, alkoxyalkyl, $COR^{10}$, $CO_2R^{10}$, $CH_2R^{10}$, or $CONHR^{10}$, where $R^{10}$ is H or optionally substituted $C_{1-6}$ alkyl; and each $R^3$ is, independently, hydroxyl, optionally substituted $C_{1-6}$ alkoxy, optionally substituted $C_{1-6}$ alkenyloxy, alkyloxyalkoxy, cyano, acyl, amino, optionally substituted alkylamino, aminoalkyl, amido, acylamino, alkylurea, alkylcarbamoyl, carboxyl, optionally substituted alkylcarboxyl, thioyl, optionally substituted alkylthio, $SO_3H$, optionally substituted alkylsulfinyl, or optionally substituted alkylsulfonyl; and n is 1-3. In some embodiments, the compound has Formula IX. In other embodiments, the compound has the formula IXa.

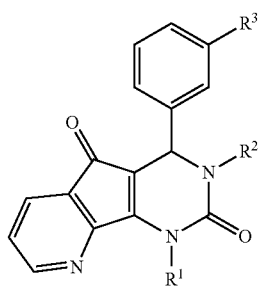

Formula IX

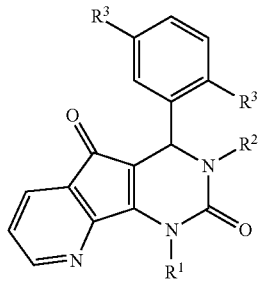

Formula IXa

In another embodiment, the invention features a compound having Formula X, or a pharmaceutically acceptable salt thereof:

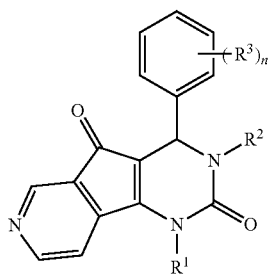

Formula X wherein each of $R^1$ and $R^2$ is, independently, H, optionally substituted $C_{1-6}$ alkyl, arylalkyl, heteroarylalkyl, alkoxyalkyl, $COR^{10}$, $CO_2R^{10}$, $CH_2CO_2R^{10}$, or $CONHR^{10}$, where $R^{10}$ is H or optionally substituted $C_{1-6}$ alkyl; each $R^3$ is, independently, hydroxyl, optionally substituted $C_{1-6}$ alkoxy, optionally substituted $C_{1-6}$ alkenyloxy, alkyloxyalkoxy, cyano, acyl, amino, optionally substituted alkylamino, aminoalkyl, amido, acylamino, alkylurea, alkylcarbamoyl, carboxyl, optionally substituted alkylcarboxyl, thioyl, optionally substituted alkylthio, $SO_3H$, optionally substituted alkylsulfinyl, or optionally substituted alkylsulfonyl; and n is 1-3. In some embodiments, the compound has Formula XI. In other embodiments, the compound has Formula XIa.

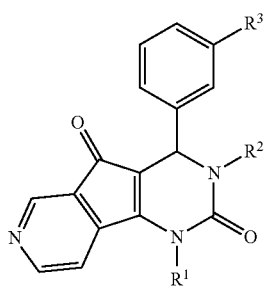

Formula XI

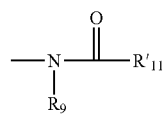

Formula XIa

Included within the scope of the invention are, for each compound described herein, the salts thereof, or a solvate, hydrate, oxidative metabolite or prodrug of the compound or its salt. When the compounds are referred to herein, it is understood that salts, solvates, hydrates, oxidative metabolites, and prodrugs of the compounds are also included. Tautomers of the compounds disclosed are also included within the scope of the invention.

Any of the compounds disclosed herein may be used to treat any diseases disclosed herein. In addition, these compounds may be used to inhibit a function of a TRPA1 channel in vitro or in vivo.

DETAILED DESCRIPTION OF THE INVENTION

Definitions

The term "acyl" refers to a group represented by the general formula hydrocarbylC(O)—, preferably alkylC(O)—.

The term "acylamino" refers to a moiety that can be represented by the general formula:

$$\mathrm{-N(R_9)-C(O)-R'_{11}}$$

wherein $R_9$ is as defined below, and $R'^{11}$ represents a hydrogen, an alkyl, an alkenyl or —$(CH_2)_m$—$R^8$, where m and $R^8$ are as defined herein.

The term "aliphatic group" refers to a straight-chain, branched-chain, or cyclic aliphatic hydrocarbon group and includes saturated and unsaturated aliphatic groups, such as an alkyl group, an alkenyl group, and an alkynyl group.

The term "alkenyl," as used herein, refers to an aliphatic group containing at least one double bond.

The terms "alkoxyl" or "alkoxy" as used herein refers to an alkyl group, as defined below, having an oxygen radical attached thereto. Representative alkoxyl groups include methoxy, ethoxy, propyloxy, tert-butoxy and the like. An "ether" is two hydrocarbons covalently linked by an oxygen.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., C1-C30 for straight chains, C3-C30 for branched chains), and more preferably 20 or fewer, and most preferably 10 or fewer. Likewise, preferred cycloalkyls have from 3-10 carbon atoms in their ring structure, and more preferably have 5, 6 or 7 carbons in the ring structure.

The term "alkynyl", as used herein, refers to an aliphatic group containing at least one triple bond.

The term "alkylurea" refers to a group having the structure —NHC(=O)NH-alkyl.

The term "alkylcarbamoyl" refers to a group having the structure —NHCO$_2$-alkyl.

The term "alkylthio" refers to a hydrocarbyl group having a sulfur radical attached thereto. In some embodiments, the "alkylthio" moiety is represented by one of —S-alkyl, —S-alkenyl, or —S-alkynyl. Representative alkylthio groups include methylthio, ethylthio, and the like.

The terms "amine" and "amino" refer to both unsubstituted and substituted amines, e.g., a moiety that can be represented by the general formula:

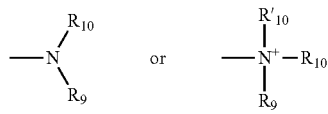

wherein $R_9$, $R_{10}$ and $R'_{10}$ each independently represent a hydrogen, an alkyl, an alkenyl, —(CH$_2$)$_m$—R$_8$, or $R_9$ and $R_{10}$ taken together with the N atom to which they are attached complete a heterocycle having from 4 to 8 atoms in the ring structure; $R_8$ represents an aryl, a cycloalkyl, a cycloalkenyl, an alkoxy, a heterocycle or a polycycle; and m is zero or an integer in the range of 1 to 8.

The term "amido" refers to a moiety that can be represented by the general formula:

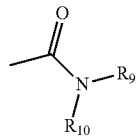

wherein $R_9$, $R_{10}$ are as defined above.

The term "aralkyl", as used herein, refers to an alkyl group substituted with an aryl group (e.g., an aromatic or heteroaromatic group).

The term "aryl" as used herein includes 5-, 6-, and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, polycyclyl, hydroxyl, alkoxyl, amino, nitro, sulfhydryl, imino, amido, phosphate, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF3, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls. Each ring can contain, e.g., 5-7 members.

The term "carbocycle or cyclyl," as used herein, refers to an aromatic or non-aromatic ring in which each atom of the ring is carbon.

The term "carbonyl" refers to moieties represented by the general formula:

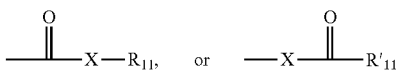

wherein X is a bond or represents an oxygen or a sulfur, and $R_{11}$ represents a hydrogen, an alkyl, an alkenyl, —(CH$_2$)$_m$—R$_8$ or a pharmaceutically acceptable counter-ion, $R'_{11}$ represents a hydrogen, an alkyl, an alkenyl or —(CH$_2$)$_m$—R$_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiocarbonyl" group. Where X is a sulfur and $R_{11}$ or $R'_{11}$ is not hydrogen, the formula represents a "thioester." Where X is a sulfur and $R_{11}$ is hydrogen, the formula represents a "thiocarboxylic acid." Where X is a sulfur and $R_{11}'$ is hydrogen, the formula represents a "thioformate." On the other hand, where X is a bond, and $R_{11}$ is not hydrogen, the above formula represents a "ketone" group. Where X is a bond, and $R_{11}$ is hydrogen, the above formula represents an "aldehyde" group.

The term "ester", as used herein, refers to a group —C(O)OR$^9$ wherein R$^9$ represents a hydrocarbyl group.

The terms "halo" and "halogen" as used herein means halogen and includes chloro, fluoro, bromo, and iodo.

The terms "hetaralkyl" and "heteroaralkyl", as used herein, refers to an alkyl group substituted with a heteroaryl group.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). Any ring atom can be substituted (e.g., by one or more substituents).

The terms "heterocyclyl" or "heterocyclic group" refer to 3- to 10-membered ring structures, more preferably 3- to 7-membered rings, whose ring structures include one to four heteroatoms. Heterocycles can also be polycycles, with each group having, e.g., 5-7 ring members. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF₃, —CN, or the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

As used herein, the term "nitro" means —NO2; the term "halogen" or "halo" designates —F, —Cl, —Br or —I; the term "sulfhydryl" means —SH; the term "hydroxyl" means —OH; and the term "sulfonyl" means —SO₂—.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —CF₃, —CN, or the like.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis,* 2$^{nd}$ ed.; Wiley: New York, 1991).

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF₃, —CN and the like. Exemplary substituted alkyls are described below. Cycloalkyls can be further substituted with alkyls, alkenyls, alkoxys, alkylthios, aminoalkyls, carbonyl-substituted alkyls, —CF₃, —CN, and the like. Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The term "sulfate" refers to a moiety that can be represented by the general formula:

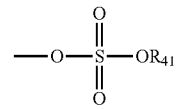

in which R41 is as defined herein.

The term "sulfonamido" refers to a moiety that can be represented by the general formula:

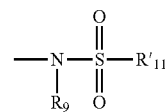

in which R₉ and R'¹¹ are as defined above.

The term "sulfonate" refers to a moiety that can be represented by the general formula:

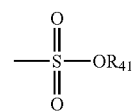

in which R41 is an electron pair, hydrogen, alkyl, cycloalkyl, or aryl.

The terms "sulfoxido" or "sulfinyl," as used herein, refers to a moiety that can be represented by the general formula —S(=O)—R44, in which R44 is selected from the group consisting of hydrogen, alkyl, alkenyl, alkynyl, cycloalkyl, heterocyclyl, aralkyl, or aryl.

The term "thioester," as used herein, refers to a group —C(O)SR⁹ or —SC(O)R⁹ wherein R⁹ represents a hydrocarbyl.

As used herein, the definition of each expression, e.g., alkyl, m, n, etc., when it occurs more than once in any structure, is intended to be independent of its definition elsewhere in the same structure.

Exemplary monocyclic rings include furan, thiophene, pyrrole, pyrroline, pyrrolodine, oxazole, thiazole, imidazole, imidazoline, pyrazole, pyrazoline, pyrazolidine, isoxazole, isothiazole, oxadiazole, triazole, thiadiazole, pyran, pyridine, piperidine, dioxane, morpholine, dithiane, thiomorpholine, pyridazine, pyrimidine, pyrazine, piperazine, triazine, and trithiane.

Exemplary bicyclic rings include indolizinyl, indolyl, isoindolyl, indolinyl, benzofuranyl, benzothiophenyl, indazolyl, benzimidazolyl, benthiazolyl, purinyl, quinolizinyl, quinolinyl, isoquinolinyl, cinnolinyl, phthalazinyl, quinazolinyl, quinoxalinyl, naphthyridinyl, pteridinyl, indenyl, naphthalenyl, azulenyl, imidazopyridazionyl, pyrazolopyrimidinedionyl, or pyrrolopyrimidinedionyl moieties.

Exemplary tricyclic rings include carbazole, acridine, phenazine, phenothiazine, phenoxazine, fluorine, and anthracene.

Certain compounds disclosed herein may exist in particular geometric or stereoisomeric forms. The present invention contemplates all such compounds, including cis- and trans-isomers, R- and S-enantiomers, diastereomers, (d)-isomers, (l)-isomers, the racemic mixtures thereof, and other mixtures thereof, as falling within the scope of the invention. For example, if one chiral center is present in a molecule, the invention includes racemic mixtures, enantiomerically enriched mixtures, and substantially enantiomerically pure compounds. The composition can contain, e.g., more than 50%, more than 60%, more than 70%, more than 80%, more than 90%, more than 95%, or more than 99% of a single enantiomer.

The "enantiomeric excess" or "% enantiomeric excess" of a composition can be calculated using the equation shown below. In the example shown below a composition contains 90% of one enantiomer, e.g., the S enantiomer, and 10% of the other enantiomer, i.e., the R enantiomer.

$$ee=(90-10)/100=80\%.$$

Thus, a composition containing 90% of one enantiomer and 10% of the other enantiomer is said to have an enantiomeric excess of 80%.

Methods of preparing substantially isomerically pure compounds are known in the art. If, for instance, a particular enantiomer of a compound disclosed herein is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts may be formed with an appropriate optically active acid or base, followed by resolution of the diastereomers thus formed by fractional crystallization or chromatographic means well known in the art, and subsequent recovery of the pure enantiomers. Alternatively, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Techniques for inverting or leaving unchanged a particular stereocenter, and those for resolving mixtures of stereoisomers are well known in the art, and it is well within the ability of one of skill in the art to choose an appropriate method for a particular situation. See, generally, Furniss et al. (eds.), *Vogel's Encyclopedia of Practical Organic Chemistry* 5$^{th}$ Ed., Longman Scientific and Technical Ltd., Essex, 1991, pp. 809-816; and Heller, *Acc. Chem. Res.* 23: 128 (1990).

Contemplated equivalents of the compounds described above include compounds which otherwise correspond thereto, and which have the same general properties thereof (e.g., the ability to inhibit TRPA1 activity), wherein one or more simple variations of substituents are made which do not adversely affect the efficacy of the compound. In general, the compounds disclosed herein may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

The compounds described herein may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds disclosed herein, whether radioactive or not, are intended to be encompassed within the scope of the present invention. For example, deuterated compounds and compounds incorporating $^{13}$C are intended to be encompassed within the scope of the invention.

Certain compounds disclosed herein can exist in unsolvated forms as well as solvated forms, including hydrated forms. In general, the solvated forms are equivalent to unsolvated forms and are encompassed within the scope of the present invention. Certain compounds disclosed herein may exist in multiple crystalline or amorphous forms. In general, all physical forms are equivalent for the uses contemplated by the present invention and are intended to be within the scope of the present invention.

As set out above, certain embodiments of the present compounds may contain a basic functional group, such as amino or alkylamino, and are, thus, capable of forming pharmaceutically acceptable salts with pharmaceutically acceptable acids. The term "pharmaceutically acceptable salts" in this respect, refers to the relatively non-toxic, inorganic and organic acid addition salts of compounds disclosed herein. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19.)

In other cases, the compounds disclosed herein may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds disclosed herein. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

The terms "antagonist" and "inhibitor" are used interchangeably to refer to an agent that decreases or suppresses a biological activity, such as to repress an activity of an ion channel, such as TRPA1. TRPA1 inhibitors include inhibitors having any combination of the structural and/or functional properties disclosed herein.

An "effective amount" of, e.g., a TRPA1 antagonist, with respect to the subject methods of inhibition or treatment, refers to an amount of the antagonist in a preparation which, when applied as part of a desired dosage regimen brings about a desired clinical or functional result. Without being bound by theory, an effective amount of a TRPA1 antagonist for use in the methods of the present invention, includes an amount of a TRPA1 antagonist effective to decrease one or more in vitro or in vivo functions of a TRPA1 channel. Exemplary functions include, but are not limited to, membrane polarization (e.g., an antagonist may promote hyperpolarization of a cell), ion flux, ion concentration in a cell, outward current, and inward current. Compounds that antagonize TRPA1 function include compounds that antagonize an in vitro or in vivo functional activity of TRPA1. When a particular functional activity is only readily observable in an in vitro assay, the ability of a compound to inhibit TRPA1 function in that in vitro assay serves as a reasonable proxy for the activity of that compound. In certain embodiments, an effective amount is an amount sufficient to inhibit a TRPA1-mediated current and/or the amount sufficient to inhibit TRPA1 mediated ion flux.

The term "preventing," when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "prodrug" is intended to encompass compounds that, under physiological conditions, are converted into the therapeutically active agents of the present invention. A common method for making a prodrug is to include selected moieties that are hydrolyzed under physiological conditions to reveal the desired molecule. In other embodiments, the prodrug is converted by an enzymatic activity in the host animal.

The terms "TRPA1", "TRPA1 protein", and "TRPA1 channel" are used interchangeably throughout the application. These terms refer to an ion channel (e.g., a polypeptide) comprising the amino acid sequence set forth in SEQ ID NO: 1, SEQ ID NO:3, or SEQ ID NO: 5 of WO 2007/073505, or an equivalent polypeptide, or a functional bioactive fragment thereof. In certain embodiments, the term refers to a polypeptide comprising, consisting of, or consisting essentially of, the amino acid sequence set forth in SEQ ID NO: 1, SEQ ID NO:3, or SEQ ID NO: 5. TRPA1 includes polypeptides that retain a function of TRPA1 and comprise (i) all or a portion of the amino acid sequence set forth in SEQ ID NO: 1, SEQ ID NO:3 or SEQ ID NO: 5; (ii) the amino acid sequence set forth in SEQ ID NO: 1, SEQ ID NO:3 or SEQ ID NO: 5 with 1 to about 2, 3, 5, 7, 10, 15, 20, 30, 50, 75 or more conservative amino acid substitutions; (iii) an amino acid sequence that is at least 70%, 75%, 80%, 90%, 95%, 96%, 97%, 98%, or 99% identical to SEQ ID NO: 1, SEQ ID NO:3 or SEQ ID NO: 5; and (iv) functional fragments thereof. Polypeptides of the invention also include homologs, e.g., orthologs and paralogs, of SEQ ID NO: 1, SEQ ID NO: 3 or SEQ ID NO: 5.

Exemplary compounds are shown below. The $IC_{50}$ values presented in Tables 1-XX were obtained from patch clamp experiments, using human TRPA1, as described in Example 2. An "A" indicates an $IC_{50}$ value less than or equal to 100 nM; a "B" indicates an $IC_{50}$ value of greater than 100 nM and less than 500 nM; a "C" indicates an $IC_{50}$ value of 500 nM to 1000 nM; a "D" indicates an $IC_{50}$ value greater than 1000 nM. Metabolic stability in rat liver microsomes can be determined using techniques described in Kuhnz et al., Drug Metabolism and Disposition (1998) Vol. 26, 1120-27. Oral bioavailability (expressed as % F) can be determined as described in Basic & Clinical Pharmacology, 8th edition, Bertram G. Katzung (editor), Lange Medical Books/McGraw-Hill, 2001.

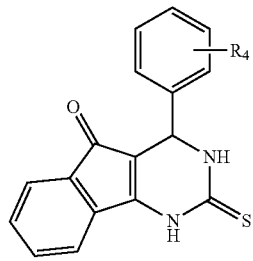

| Compound ID | R4 | Activity |
| --- | --- | --- |
| 1 | 3-OCH2cPr | A |
| 2 | 3-OCH2CH=CH2 | A |
| 3 | 3-OEt | A |
| 4 | 3-OCF2H | A |
| 5 | 3-OMe | A |
| 6 | 3-OCH2CH2OCH3 | A |
| 7 | 2-OH-5-OMe | A |
| 8 | 2-F-5-OMe | A |
| 9 | 2-Br | A |
| 10 | 2-Br-5-OMe | A |
| 11 | 3-Cl | A |
| 12 | 3-CN | A |
| 13 | H | A |
| 14 | 2-F-5-Cl | A |
| 15 | 2-OH | A |
| 16 | 2,6-diCl | B |
| 17 | 3,5-diOMe | B |
| 18 | 2,3-diCl | B |
| 19 | 2-Br-5-OH | B |
| 20 | 2-F | B |
| 21 | 3-NO2 | B |
| 22 | 3-OCH2CH2CH2OCH3 | B |
| 23 | 3-OCH2O-4 | B |
| 24 | 3,4,5-triF | B |
| 25 | 3-OCF3 | B |

-continued

| Compound ID | R4 | Activity |
|---|---|---|
| 26 | 3-OH | B |
| 27 | 2,3-naphthalene | B |
| 28 | 2-CF3 | B |
| 29 | 4-OMe | B |
| 30 | 3-OCH2CH2OH | B |
| 31 | 2-Et | B |
| 32 | 3-F-4-Cl | B |
| 33 | 3-Py* | C |
| 34 | 3,4-diCl | C |
| 35 | 4-CN | C |
| 36 | 2-Cl | C |
| 37 | 4-NO2 | C |
| 38 | 4-Me | D |
| 39 | 3-Br-4-OMe | D |
| 40 | 2-OMe | D |
| 41 | 4-F | D |
| 42 | 2,5-diOMe | D |
| 43 | 2-OEt | D |
| 44 | 3-OMe-4-OH | D |
| 45 | 3,4-diF | D |
| 46 | 4-heptanyl | D |
| 47 | 3-OBu | D |
| 48 | 3-OiPr | D |
| 49 | 4-NMe2 | D |
| 50 | 3-OCH2CH2NMe2 | D |
| 51 | 3-OCH2CH2NH2 | D |
| 52 | 2-OCH2CH=CH2 | |
| 53 | 4-Cl | |

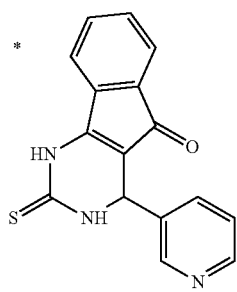 [SMILES: O=C1C2=C(NC(=S)NC2c2cccnc2)c2ccccc21]

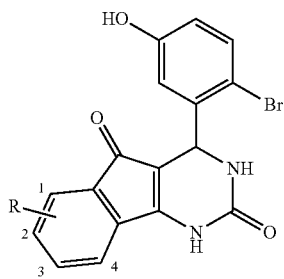

| Compound ID | R | Activity |
|---|---|---|
| 101 | 1-Cl | A |
| 102 | H | B |
| 103 | 2-Cl | D |
| 104 | 1-OH | D |
| 105 | 2-OH | D |
| 106 | 3-OH | D |
| 107 | 2-Me | C |

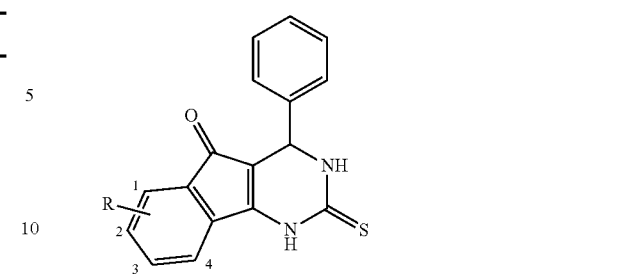

| Compound ID | R | Activity |
|---|---|---|
| 201 | H | A |
| 202 | 1-OH | D |
| 203 | 2-OH | D |
| 204 | 3-OH | D |
| 205 | 3-OMe | B |

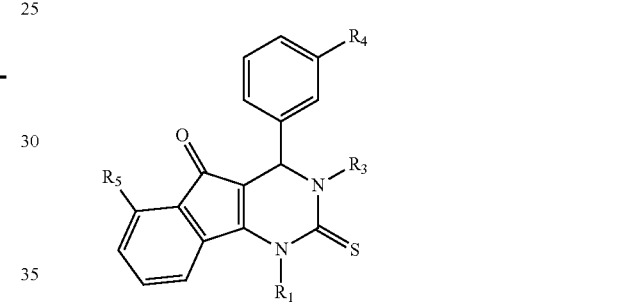

| Compound ID | R1 | R3 | R4 | R5 | Activity |
|---|---|---|---|---|---|
| 301 | H | H | H | H | A |
| 302 | Me | H | H | H | A |
| 303 | H | Me | H | H | D |
| 304 | Me | Me | H | H | D |
| 305 | H | H | OCH2CH=CH2 | H | A |
| 306 | Me | H | OCH2CH=CH2 | H | A |
| 307 | H | H | CN | H | A |
| 308 | Me | H | CN | H | A |
| 309 | H | Me | CN | H | D |
| 310 | H | H | OEt | H | A |
| 311 | Me | H | OEt | H | A |
| 312 | H | H | H | OH | |
| 313 | Me | H | H | OH | D |

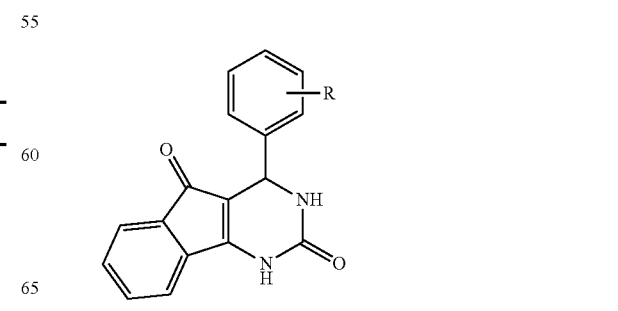

| Compound ID | R | Activity |
|---|---|---|
| 401 | 2-F-3-OCH2CH=CH2 | A |
| 402 | 3-CHFCH2CH=CH2 | A |
| 403 | 3-F-5-OCH2CH=CH2 | A |
| 404 | 2,5-diF-3-OPr | A |
| 405 | 3-OCH2CH=CH2 | A |
| 406 | 3-Cl-5-OCH2CH=CH2 | A |
| 407 | 3-OPr | A |
| 408 | 3-OBu | A |
| 409 | 2-F-3-OEt | A |
| 410 | 2-F-3-OPr | A |
| 411 | 2-Cl-3-OCH2CH=CH2 | A |
| 412 | 3-OEt | B |
| 413 | 3-OCH2CF3 | B |
| 414 | 3-OCF2H | B |
| 415 | 2-Cl-5-OCH2CH=CH2 | B |
| 416 | 3-OCH2C≡CH | B |
| 417 | 2-F-5-OCH2CH=CH2 | B |
| 418 | 3-OCH2CH2CH2OMe | B |
| 419 | 2-Cl, 3-OCH2(c-Pr) | B |
| 420 | 2,6-DiF-3-OEt | B |
| 421 | 2-Me-3-OCH2CH=CH2 | B |
| 422 | 3-OCH2cPr | B |
| 423 | 2-Cl-3-OEt | C |
| 424 | 3-OMe | C |
| 425 | 3-OCH2CN | C |
| 426 | 2-Cl | C |
| 427 | 3-Bu | C |
| 428 | 2-Cl-3-OMe | D |
| 429 | 2-Cl-5-OMe | D |
| 430 | 3-CN | D |
| 431 | 3-Cl | D |
| 432 | 2-F-5-OMe | D |
| 433 | 2-Br-5-OMe | D |
| 434 | H | D |
| 435 | 2-OH | D |
| 436 | 3-OH | D |
| 437 | 3-OiPr | D |
| 438 | 2,3-diOMe | D |
| 439 | 2-OCH2O-3- | D |
| 440 | 2-OCF2O-3- | D |
| 441 | 2,5-diOMe | D |
| 442 | 4-Cl | D |
| 443 | 3-N(Et)Ac | D |
| 444 | 3-NH2 | D |
| 445 | 3-NMe2 | D |
| 446 | 2,3-diCl | D |
| 447 | 2-F | D |
| 448 | 2-Cl-5-CF3 | D |
| 449 | 2,6-di-Cl | D |
| 450 | 3-OCF2CH3 | D |
| 451 | 3-OCF2CHF2 | D |
| 452 | 3-CF3 | D |
| 453 | 3-CH2OCH3 | D |
| 454 | 2-CF3-3-OCH2CH=CH2 | D |
| 455 | 2-OMe-3-OCH2CH=CH2 | D |
| 456 | 2-OH-3-OCH2CH=CH2 | D |
| 457 | 3-OCH2O-4 | D |
| 458 | 3,5-diOMe | D |
| 459 | 3-OC(O)cPr | D |
| 460 | 3-O-(n-pentyl) | D |
| 461 | 3-OCH2(c-Bu) | D |
| 462 | 3-OCH2CH2OMe | B |

| Compound ID Number | R | Activity |
|---|---|---|
| 501 | 3-pyridyl | D |
| 502 | 2-thienyl | D |
| 503 | 5-ethoxy-3-pyridyl | D |
| 504 | 6-ethoxy-2-pyridyl | C |
| 505 | benzoxazol-2(3H)-one-7-yl | D |
| 506 | 3-ethyl-benzoxazol-2(3H)-one-7-yl | D |
| 507 | benzimidazol-2(3H)-one-4-yl | D |

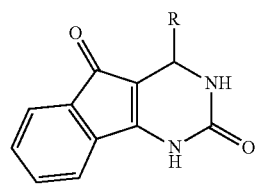

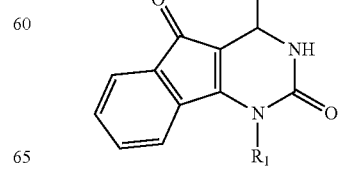

| Compound ID | R4 | R1 | Activity |
| --- | --- | --- | --- |
| 601 | 3-OEt | CH2CN | A |
| 602 | 3-OEt | H | B |
| 603 | 3-OEt | Me | A |
| 604 | 3-OEt | Et | A |
| 605 | 3-OEt | CH2CF3 | C |
| 606 | 3-OEt | Bn | A |
| 607 | 3-OEt | CH2(4-F-Ph) | B |
| 608 | 3-OEt | CH2CO2Et | A |
| 609 | 3-OEt | CH2CO2tBu | C |
| 610 | 3-OEt | CH2CO2H | D |
| 611 | 3-OEt | CH2(2-Py) | D |
| 612 | 3-OEt | CH2(3-Py) | B |
| 613 | 3-OEt | CH2(4-Py) | D |
| 614 | 3-OEt | CH2CH=CH2 | B |
| 615 | 3-OPr | CH2CN | A |
| 616 | 2-F-3-OEt | H | A |
| 617 | 2-F-3-OEt | CH2CN | A |
| 618 | 3-OCF2H | H | B |
| 619 | 3-OCF2H | CH2CN | A |
| 620 | 3-OCF2H | Et | B |
| 621 | 3-OMe | Bn | A |
| 622 | 3-OMe | H | C |
| 623 | 3-OMe | Me | B |
| 624 | 3-OMe | Et | B |
| 625 | 3-OMe | Pr | D |
| 626 | 3-OMe | Bn | B |
| 627 | 3-OMe | CH2CH2OH | D |
| 628 | 3-OMe | CH2CH2OCH3 | B |
| 629 | 3-OCH2CH=CH2 | CH2CH2NMe2 | D |
| 630 | 3-OCH2CH=CH2 | Me | A |
| 631 | 3-OCH2CH=CH2 | Et | A |
| 632 | 3-OCH2CH=CH2 | CH2CO2Et | A |
| 633 | 3-OCH2CH=CH2 | Bn | A |
| 634 | 3-OCH2CH=CH2 | CH2(4-F-Ph) | A |
| 635 | 3-OCH2CH=CH2 | CH2(3-Py) | A |
| 636 | 3-OCH2CH=CH2 | CH2(4-Py) | D |
| 637 | 2-Cl-5-OCH2CH=CH2 | CH2(2-Py) | B |
| 638 | 2-Cl-5-OCH2CH=CH2 | H | B |
| 639 | 2-Cl-3-OCH2CH=CH2 | Me | A |
| 640 | 2-Cl-3-OCH2CH=CH2 | Me | A |
| 641 | 3-OCH2cPr | H | A |
| 642 | 2-CF3-3-OCH2CH=CH2 | Me | B |
| 643 | 2-CF3-3-OCH2CH=CH2 | H | D |
| 644 | 3-CN | Me | D |
| 645 | 3-OPr | Me | D |
| 646 | 3-OPr | Me | A |
| 647 | 3-OPr | Et | A |
| 648 | 2,6-DiF-3-OPr | Bn | A |
| 649 | 3-OCF2CH=CH2 | CH2CN | A |
| | | Bn | D |

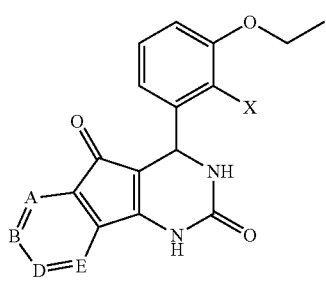

| Compound ID | Substituents | Activity |
| --- | --- | --- |
| 800 | A = CH | B |
| | B = CH | |
| | D = CH | |
| | E = N | |

| Compound ID | Substituents | Activity |
| --- | --- | --- |
| | X = F | |
| 801 | A = N | D |
| | B = CH | |
| | D = CH | |
| | E = CH | |
| | X = F | |
| 802 | A = CH | B |
| | B = CH | |
| | D = CH | |
| | E = N | |
| | X = H | |
| 803 | A = N | D |
| | B = CH | |
| | D = CH | |
| | E = CH | |
| | X = H | |
| 804 | A = CH | C |
| | B = CH | |
| | D = N | |
| | E = CH | |
| | X = H | |
| 805 | A = CH | B |
| | B = N | |
| | D = CH | |
| | E = CH | |
| | X = H | |
| 806 | A = N | C |
| | B = CH | |
| | D = CH | |
| | E = N | |
| | X = H | |

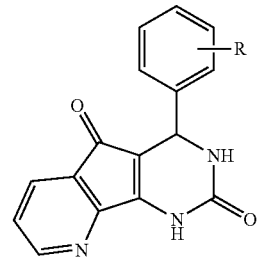

| Compound ID | R | Activity | RLM T1/2 (min) |
| --- | --- | --- | --- |
| 901 | 2-F-3-OEt | B | A |
| 902 | 3-OEt | B | A |
| 903 | 3-Bu | B | |
| 904 | 3-OPr | A | |
| 905 | 3-CHFCH2CH=CH2 | A | A |
| 906 | 3-SPr | B | A |
| 907 | 3-CHFPr | A | A |
| 908 | 3-CH(OH)Pr | B | A |
| 909 | 3-C(=O)Pr | B | A |
| 910 | 3-S(=O)Pr | D | |
| 911 | 3-S(=O)2Pr | D | |
| 912 | 2,6-DiF-3-OPr | A | |
| 913 | OCH2CH2CH2OMe | | |

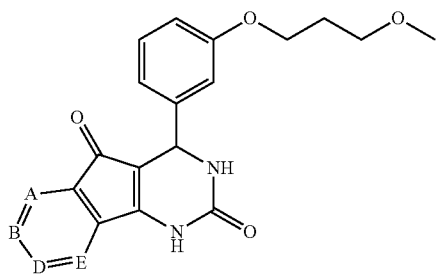
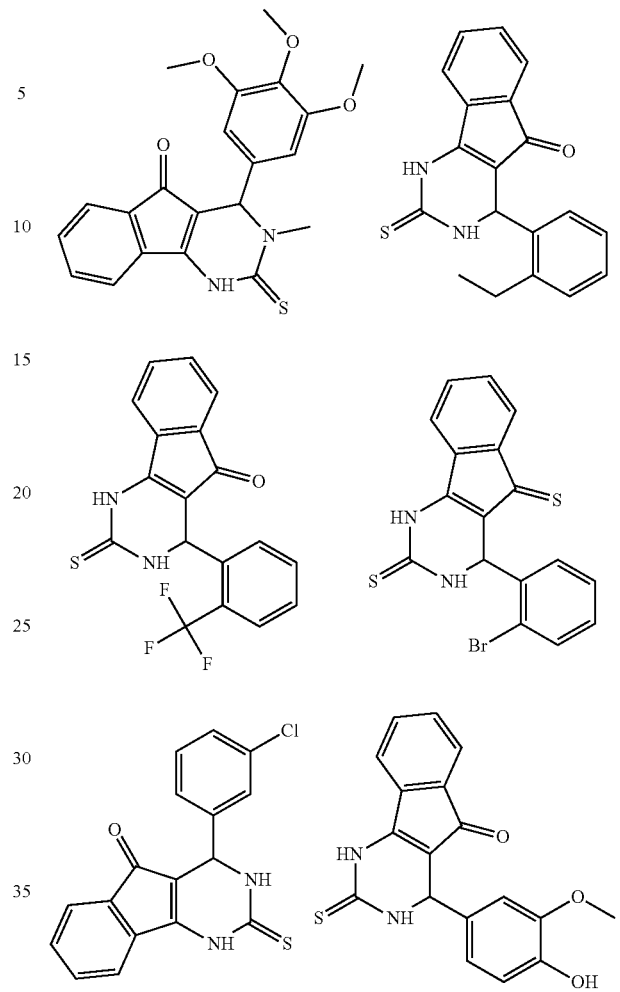
| Compound ID | Substituents | Activity |
|---|---|---|
| 914 | A = CH<br>B = CH<br>D = CH<br>E = CH | B |
| 915 | A = N<br>B = CH<br>D = CH<br>E = CH | D |
| 916 | A = CH<br>B = N<br>D = CH<br>E = CH | D |
| 917 | A = CH<br>B = CH<br>D = N<br>E = CH | D |
| 918 | A = CH<br>B = CH<br>D = CH<br>E = N | D |
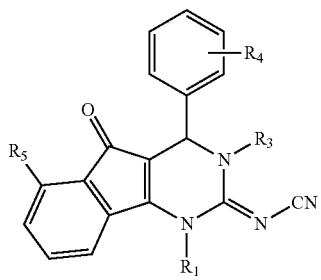
| Compound ID | R4 | R1 | R3 | R5 | Activity |
|---|---|---|---|---|---|
| 950 | 3-OCH2CH=CH2 | H | H | H | D |
| 951 | 3-OCH2cPr | H | H | H | D |
| 952 | 3-OCH2cPr | H | Me | H | D |
| 953 | 3-OCH2cPr | H | Me | Cl | D |
| 954 | 3-OCH2cPr | H | H | Cl | D |
| 955 | 3-CN | H | H | H | D |
| 956 | H | H | H | H | D |
| 957 | 2-Cl-3-OCH2cPr | H | H | H | D |
| 958 | 3-OCH2cBu | H | H | H | D |
| 959 | 3-OiBu | H | H | H | D |
| 960 | 3-OPr | H | H | H | D |
| 961 | 3-OCH2CH=CH2 | Bn | H | H | D |
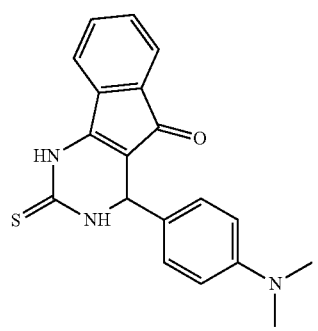
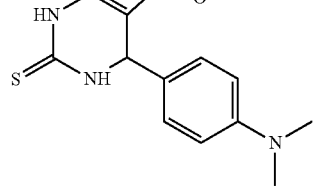

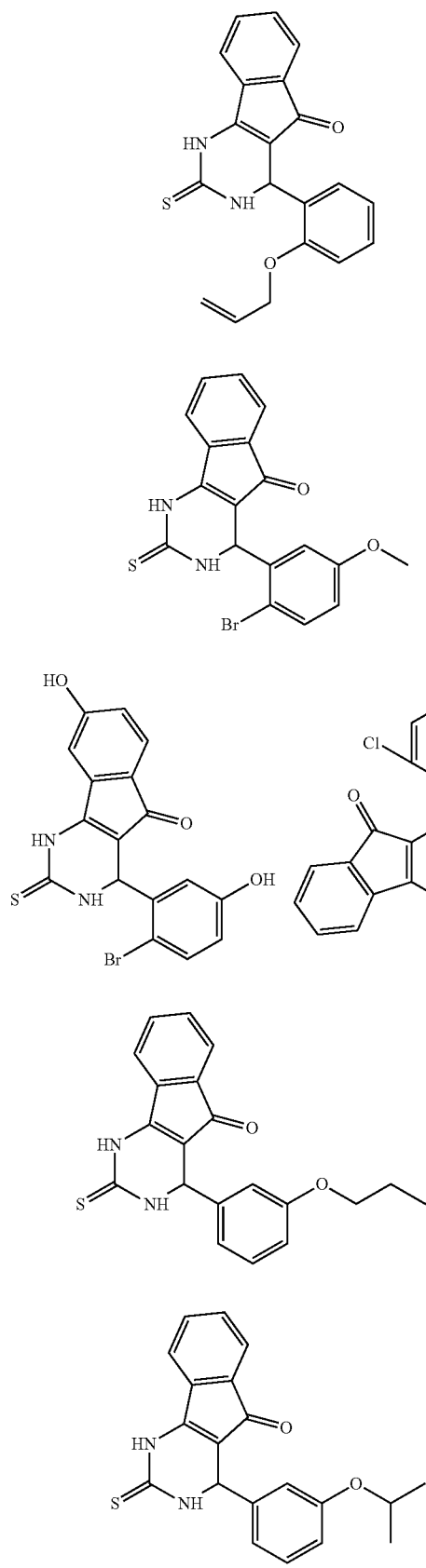
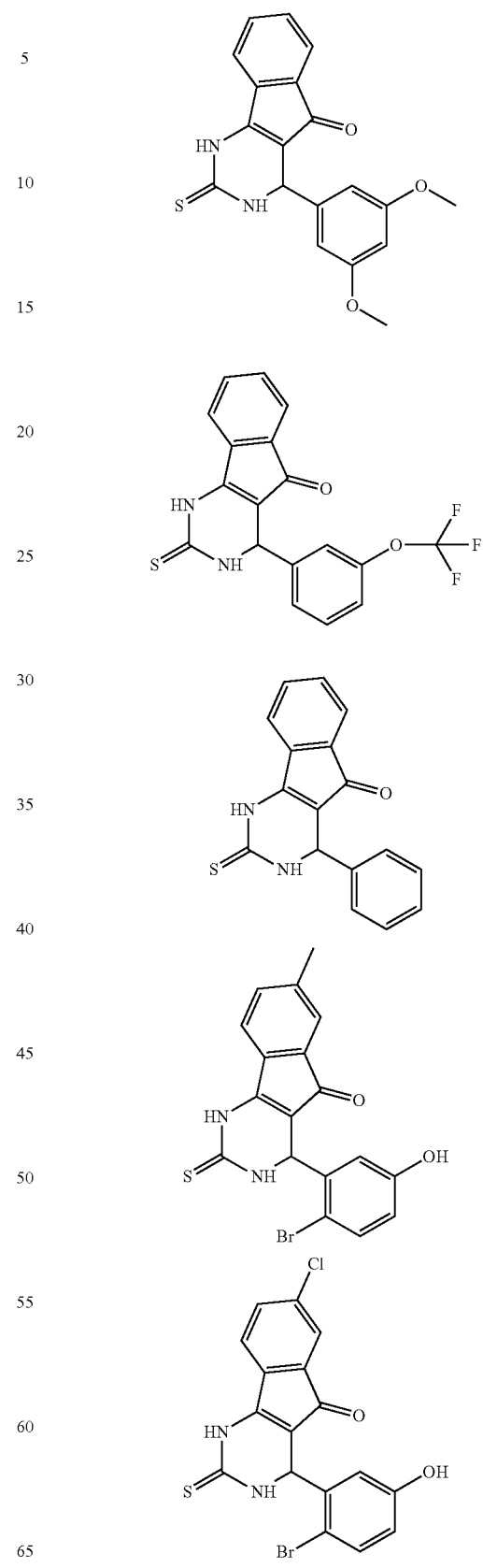

-continued
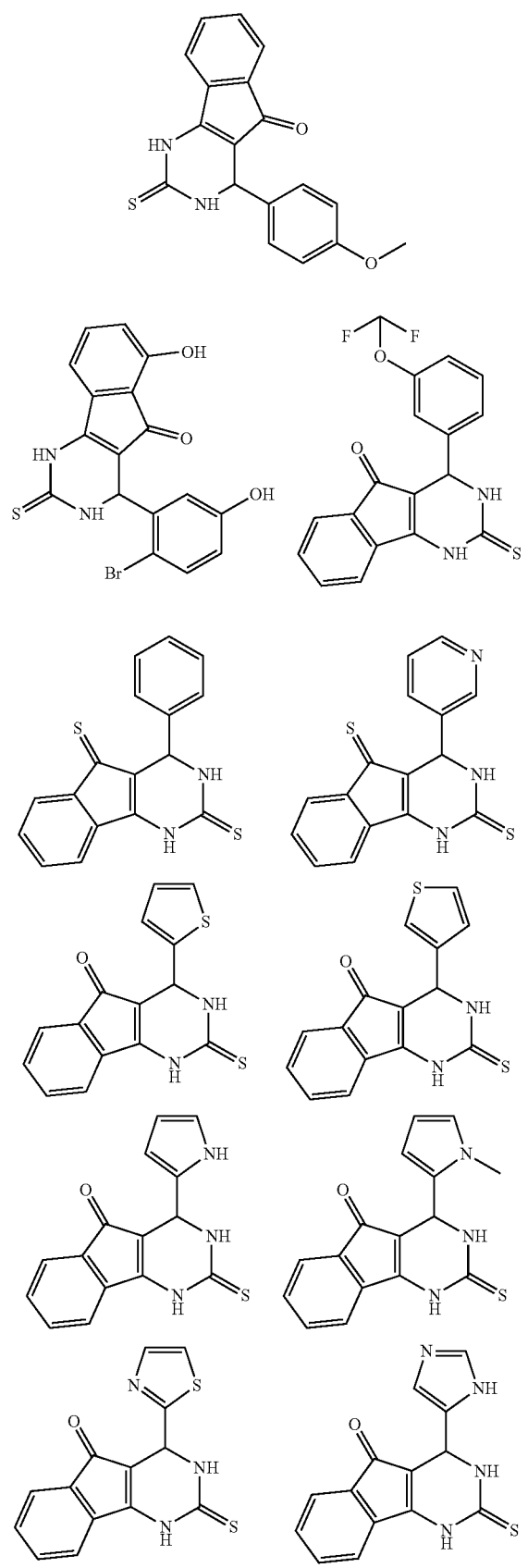
-continued
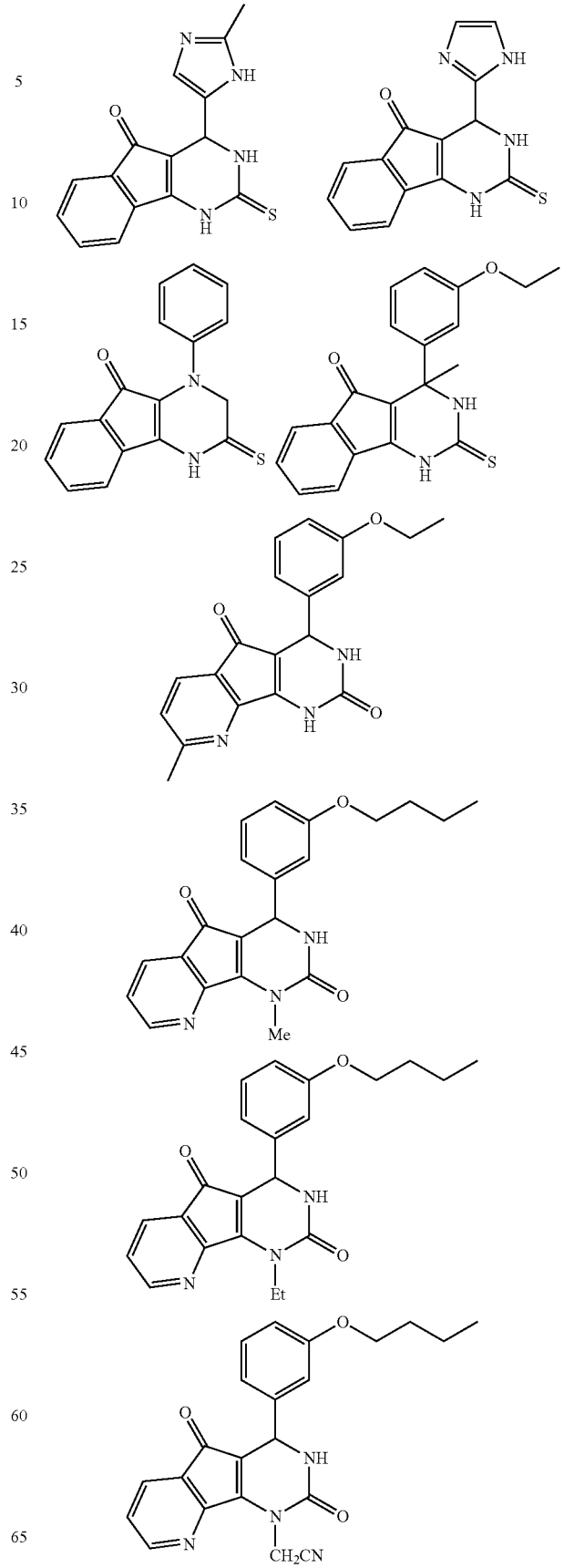

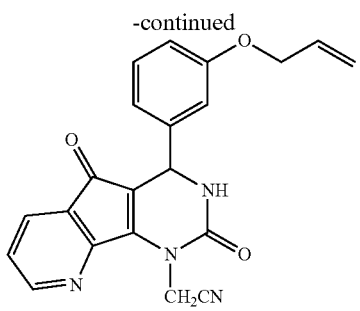

It is believed that the more potent enantiomer is the beta form, which has the R configuration in the compound shown immediately below.

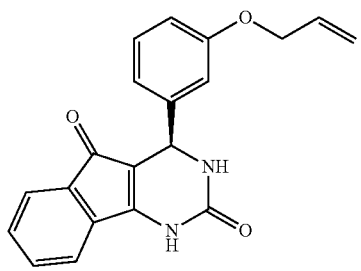 [SMILES: C=CCOc1cccc([C@H]2NC(=O)NC3=C2C(=O)c2ccccc23)c1]

For each compound disclosed herein, it is believed that the enantiomeric form having the stereochemistry illustrated above is more active than the other enantiomer. The enantiomerically pure compounds were prepared by separating the racemic mixture on a chiral column or by converting the racemic mixture into a mixture of diastereomers using an auxiliary chiral moiety, separating the diastereomers on a non-chiral column, then hydrolyzing to remove the auxiliary chiral moiety.

Indications

Cellular homeostasis is a result of the summation of regulatory systems involved in, amongst other things, the regulation of ion flux and membrane potential. Cellular homeostasis is achieved, at least in part, by movement of ions into and out of cells across the plasma membrane and within cells by movement of ions across membranes of intracellular organelles including, for example, the endoplasmic reticulum, sarcoplasmic reticulum, and mitochondria and endocytic organelles including endosomes and lysosomes.

Movement of ions across cellular membranes is carried out by specialized proteins. TRP channels are one large family of non-selective cation channels that function to help regulate ion flux and membrane potential. TRP channels are subdivided into 6 sub-families including the TRPA (ANKTM1) family, and TRPA1 is a member of the TRPA class of TRP channels.

Non-selective cation channels such as TRPA1 modulate the flux of calcium and sodium ions across cellular membranes. Sodium and calcium influx leads to depolarization of the cell. This increases the probability that voltage-gated ion channels will reach the threshold required for activation. As a result, activation of non-selective cation channels can increase electrical excitability and increase the frequency of voltage-dependent events. Voltage-dependent events include, but are not limited to, neuronal action potentials, cardiac action potentials, smooth muscle contraction, cardiac muscle contraction, and skeletal muscle contraction.

Calcium influx caused by the activation of non-selective cation channels such as TRPA1 also alters the intracellular free calcium concentration. Calcium is a ubiquitous second messenger molecule within the cell, so alterations in intracellular calcium levels have profound effects on signal transduction and gene expression. As a result, activation of non-selective cation channels such as TRPA1 can lead to changes in gene expression and cellular phenotype. Gene expression events include, but are not limited to, production of mRNAs encoding cell surface receptors, ion channels, and kinases. These changes in gene expression can lead to hyperexcitability in that cell.

TRPA1 proteins are broad receptors for noxious chemicals, both endogenous and exogenous. They respond to any of a variety of stimuli that can induce cysteine modification (Hinman et al., 2006; MacPherson et al. 2007). In addition TRPA1 can function as a receptor operated channel. It expressed in sensory neurons (see, e.g., Jordt et al. (2004) Nature 427:260-265) including those with cell bodies residing in the dorsal root ganglion, trigeminal ganglion, and nodose ganglia (see Jordt et al. (2004) Nature 427:260-265, Nagata et al. (2005) J. Neurosci 25(16) 4052-61). In addition, low levels of TRPA1 message can be found in some types of fibroblasts (see Jaquemar et al. (1999) JBC 274(11): 7325-33). TRPA1 has also been reported to be expressed in the bladder. Stimulation of a number of extracellular receptors, including, but not limited to, G-protein coupled receptors or receptor tyrosine kinases are sufficient to activate TRPA1.

Modulating the function of TRPA1 proteins provides a means of modulating calcium homeostasis, sodium homeostasis, membrane polarization, and/or intracellular calcium levels, and compounds that can modulate TRPA1 function are useful in many aspects, including, but not limited to, maintaining calcium homeostasis, modulating intracellular calcium levels, modulating membrane polarization, and treating or preventing diseases, disorders, or conditions associated with calcium and/or sodium homeostasis or dyshomeostasis.

Thus, TRPA1 antagonists can be used as part of a prophylaxis or treatment for a variety of disorders and conditions, described in more detail below. In other embodiments, the invention provides methods and compositions for inhibiting a function of a TRPA1 channel in vitro or in vivo. The compounds described herein can be used in the treatment of any of the foregoing or following diseases or conditions, including in the treatment of pain associated with any of the foregoing or following diseases or conditions.

Treatment of Pain, Sensitivity to Pain and Touch, or Pain-Related Diseases or Disorders In certain embodiments, the TRPA1 inhibitor is used to treat or ameliorate pain. Exemplary classes of pain that can be treated using a TRPA1 inhibitor include, but are not limited to nociceptive pain, inflammatory pain, and neuropathic pain. The pain can be chronic or acute.

As outlined above, TRPA1 inhibitors may be particularly useful in the treatment of pain associated with cancer, osteoarthritis, rheumatoid arthritis, post-herpetic neuralgia, burns, and other indications detailed above. To further illustrate, additional exemplary indications for which compounds disclosed herein can be used include oral pain, pelvic pain, Fabry's disease, complex regional pain syndrome, pancreatitis, and fibromyalgia syndrome.

Fabry's Disease

Vague complaints of pain in hands and feet may be a presenting feature. These symptoms are called acroparesthesias, as they reflect the peripheral neuropathy that is a frequent manifestation of the disease. This pain may be both episodic and chronic. Acute episodes may be triggered by exposure to extremes of temperature, stress, emotion, and/or fatigue.

The compounds disclosed herein may also be used in connection with prevention or treatment of sensitivity to pain and touch. Pain or sensitivity to pain and touch may be indicated in a variety of diseases, disorders or conditions, including, but not limited to, diabetic neuropathy, breast pain, psoriasis, eczema, dermatitis, burn, post-herpetic neuralgia (shingles), nociceptive pain, peripheral neuropathic and central neuropathic pain, chronic pain, cancer and tumor pain, spinal cord injury, crush injury and trauma induced pain, migraine, cerebrovascular and vascular pain, sickle cell disease pain, rheumatoid arthritis pain, musculoskeletal pain including treating signs and symptoms of osteoarthritis and rheumatoid arthritis, orofacial and facial pain, including dental, temperomandibular disorder, and cancer related, lower back or pelvic pain, surgical incision related pain, inflammatory and non-inflammatory pain, visceral pain, psychogenic pain and soft tissue inflammatory pain, fibromyalgia-related pain, and reflex sympathetic dystrophy, and pain resulting from kidney stones or urinary tract infection.

Oral pain is a particular category of pain that may be treated using the TRPA1 inhibitors disclosed herein. The term "oral pain" refers to any pain in the mouth, throat, lips, gums, teeth, tongue, or jaw. The term is used regardless of the cause of the pain and regardless of whether the oral pain is a primary or secondary symptom of a particular disease, injury, or condition.

Oral pain has a large number of possible causes. In certain embodiments, oral pain is caused by an injury or disease of the mouth, jaw, teeth, gums, throat, lips, or tongue. In certain other embodiments, oral pain is a consequence of an injury or disease that primarily affects another part of the body. In still other embodiments, oral pain is a side effect of a therapy used to treat an injury or disease of the mouth or another part of the body. TRPA1 inhibitors are useful in treating oral pain regardless of its cause.

In certain embodiments, oral pain is caused by ulcers, sores, or other lesions in the mouth. For example, oral pain may be caused by ulcers, sores, or other lesions on the tongue, gums, lips, throat, or other tissues of the mouth. Alternatively or additionally, oral pain may be caused by inflammation of the throat, tongue, gums, lips, or other tissues of the mouth. Inflammation may accompany ulcers or other lesions, or inflammation may occur prior to or in the absence of formation of ulcers or other lesions.

The foregoing are merely exemplary of diseases and conditions that cause or lead to inflammation, lesions, ulcers, or other sources of oral pain. In other embodiments, the oral pain is due to an injury to the mouth, jaw, lips, gums, or teeth. In other embodiments, the oral pain is due to oral surgery, for example, surgery for cancer, tooth extraction, or jaw remodeling. Other conditions that may lead to oral ulcers, and thus oral pain, include, but are not limited to chickpox, herpes zoster, infectious mononucleosis, syphilis, tuberculosis, acute necrotizing gingivitis, and burning mouth syndrome.

Fibromyalgia (FMS; fibromyalgia syndrome) is a widespread musculoskeletal pain and fatigue disorder. Fibromyalgia is characterized by pain in the muscles, ligaments, and tendons. The condition affects more women than men, and occurs in people of all ages. Overall, FMS is estimated to afflict 3-6% of the population. Patients have described the pain associated with fibromyalgia as deep muscular aching, throbbing, shooting, and stabbing. The pain sometimes includes an intense burning sensation. The pain and stiffness are often worse in the morning or after repetitive use of a particular muscle group.

Additionally, varying levels of fatigue ranging from mild to incapacitating are often associated with fibromyalgia. Other symptoms of fibromyalgia include gastrointestinal symptoms. Irritable bowel syndrome and IBS-like symptoms such as constipation, diarrhea, frequent abdominal pain, abdominal gas, and nausea occur in roughly 40 to 70% of FMS patients. Acid reflux or gastroesophogeal reflux disease (GERD) occurs at a similar frequency.

Another frequent and debilitating symptom of FMS is chronic headaches, including migraine and tension-type headaches. Such headaches are experienced by approximately 70% of FMS patients. Additionally, FMS patients often experience temporomandibular joint dysfunction syndrome (also known as TMJ) which produces pain in the jaw, teeth, and mouth. TMJ may also exacerbate headaches. Other common symptoms of FMS include, but are not limited to, premenstrual syndrome and painful periods; chest pain; morning stiffness; cognitive or memory impairment; numbness and tingling sensations; muscle twitching; irritable bladder; the feeling of swollen extremities; skin sensitivities; dry eyes and mouth; dizziness; and impaired coordination. Additionally, patients are often sensitive to odors, loud noises, and bright lights.

The impact of FMS on the patient is directly correlated with the level of pain and fatigue. Pain may be so severe as to interfere with normal work or family functioning. There is currently no cure for FMS, and current therapies focus primarily on improving sleep (to decrease fatigue) and treating pain. Compounds disclosed herein could be used to help manage the pain associated with FMS. Such pain includes, but is not limited to, oral pain in the jaw, teeth, and mouth. Such pain also includes non-oral musco-skeletal pain, pain due to headaches, and pain due to gastrointestinal symptoms.

Complex Regional Pain Syndrome (CRPS; also known as chronic regional pain syndrome) is a chronic pain condition. CRPS was formerly known as reflex sympathetic dystrophy (RSD). CRPS is a chronic, painful, and progressive neurological condition that affects skin, muscles, joints, and bones. The syndrome usually develops in an injured limb, such as a broken leg or following surgery. However, many cases involve only a minor injury, such as a sprain, and somtimes no precipitating injurious event can be identified. CRPS involves continuous, intense pain that is disproportionate to the severity of the injury. The pain worsens, rather than improves, over time.

The compounds disclosed herein can also be used to treat endometriosis and the pain associated therewith.

In addition, pain associated with cancer or with cancer treatment is a significant cause of chronic pain. Cancers of the bone, for example, osteosarcoma, are considered exceptionally painful, and patients with advanced bone cancer may require sedation to tolerate the intense and persistent pain. Accordingly, TRPA1 antagonists of the invention represent a significant possible therapeutic for the treatment of pain, for example, the pain associated with cancer or with cancer treatment.

Respiratory Disorders

The compounds described herein are useful for the treatment or prevention of respiratory conditions. Such conditions affect the lung, pleural cavity, bronchial tubes, trachea, upper respiratory tract as well as the nerves and muscles involved in breathing. Respiratory diseases that may be treated with the compounds described herein include obstructive diseases such as chronic obstructive pulmonary disease (COPD), emphysema, chronic bronchitis, asthma (including asthma caused by industrial irritants), cystic fibrosis, bronchiectasis, bronchiolitis, allergic bronchopulmonary aspergillosis, and tuberculosis; restrictive lung disease including asbestosis, radiation fibrosis, hypersensitivity pneumonitis, infant respiratory distress syndrome, idiopathic pulmonary fibrosis, idiopathic pulmonary fibrosis, idiopathic interstial pneumonia sarcoidosis, eosinophilic pneumonia, lymphangioleiomyomatosis, pulmonary Langerhan's cell histiocytosis, and pulmonary alveolar proteinosis; respiratory tract infections including upper respiratory tract infections (e.g., common cold, sinusitis, tonsillitis, pharyngitis and laryngitis) and lower respiratory tract infections (e.g., pneumonia); respiratory tumors whether malignant (e.g., small cell lung cancer, non-small cell lung cancer, adenocarcinoma, squamous cell carcinoma, large cell undifferentiated carcinoma, carcinoid, mesothelioma, metastatic cancer of the lung, metastatic germ cell cancer, metastatic renal cell carcinoma) or benign (e.g., pulmonary hamartoma, congenital malformations such as pulmonary sequestration and congenital cystic adenomatoid malformation (CCAM)); pleural cavity diseases (e.g., empyema and mesothelioma); and pulmonary vascular diseases (e.g, pulmonary embolism such as thromboembolism, and air embolism (iatrogenic), pulmonary arterial hypertension, pulmonary edema, pulmonary hemorrhage, inflammation and damage to capillaries in the lung resulting in blood leaking into the alveoli. Other conditions that may be treated include disorders that affect breathing mechanics (e.g., obstructive sleep apnea, central sleep apnea, amyotrophic lateral sclerosis, Guillan-Barre syndrome, and myasthenia gravis). The present compounds can also be useful for treating, reducing, or preventing one or more symptoms associated with respiratory conditions including, for example, shortness of breath or dyspnea, cough (with or without the production of sputum), coughing blood (haemoptysis), chest pain including pleuritic chest pain, noisy breathing, wheezing, and cyanosis. Other conditions include allergy-induced cough and angiotensin converting enzyme inhibitor (ACEI) induced cough.

Dermatological Diseases or Disorders

Influx of calcium across plasma membrane of skin cells is a critical signaling element involved in cellular differentiation in the skin epidermis (Dotto, 1999 Crit Rev Oral Biol Med 10:442-457). Regulating or modulating the calcium entry pathway, and thus a critical control point for skin cell growth, can treat or prevent skin diseases or disorders that are characterized by epidermal hyperplasia, a condition in which skin cells both proliferate too rapidly and differentiate poorly. Such diseases include psoriasis, and basal and squamous cell carcinomas.

Psoriasis, estimated to affect up to 7 million Americans, afflicts sufferers with mild to extreme discomfort, enhanced susceptibility to secondary infections, and psychological impact due to disfigurement of the affected areas (Lebwohl and Ali, 2001 J Am Acad Dermatol 45:487-498). Basal cell carcinomas (BCC) and squamous cell carcinomas (SCC) of the skin represent at least one-third of all cancers diagnosed in the United States each year. More than 1 million new cases are reported annually and incidence is increasing. Despite being relatively non-aggressive, slow-growing cancers, BCCs are capable of significant local tissue destruction and disfigurement. SCCs are more aggressive and thus present even greater complications.

Many dermatological disorders are accompanied by itch (pruritus). Pruritus and pain share many mechanistic similarities. Both are associated with activation of C-fibers, both are potentiated by increases in temperature and inflammatory mediators and both can be quelled with opiates. Decreasing neuronal excitability, particularly C-fiber excitability may alleviate pruritus associated with dialysis, dermatitis, pregnancy, poison ivy, allergy, dry skin, chemotherapy and eczema.

Neurological or Neurodegenerative Diseases and Disorders

Neurodegenerative diseases and disorders include but are not limited to Alzheimer's disease (AD), Parkinson's disease, Huntington's disease, amyotrophic lateral sclerosis (ALS), and other brain disorders caused by trauma or other insults including aging.

Mechanisms associated with calcium signaling may be altered in many neurodegenerative diseases and in disorders resulting from brain injury. For example, fibroblasts or T-lymphocytes from patients with AD have consistently displayed an increase in $Ca^{2+}$ release from intracellular stores compared to controls (Ito et al. (1994) Proc. Natl. Acad. Sci. U.S.A. 91:534-538; Gibson et al. (1996) Biochem. Biophys. ACTA 1316:71-77; Etchenberrigaray et al. (1998) Neurobiology of Disease, 5:37-45). Consistent with these observations, mutations in presenilin genes (PS1 or PS2) associated with familial AD (FAD) have been shown to increase InsP3-mediated $Ca^{2+}$ release from internal stores (Guo et al. (1996) Neuro Report, 8:379-383; Leissring et al. (1999) J. Neurochemistry, 72:1061-1068; Leissring et al. (1999) J. Biol. Chem. 274(46): 32535-32538; Leissring et al. (2000) J. Cell Biol. 149(4):793-797; Leissring et al. (2000) Proc. Natl. Acad. Sci. U.S.A. 97(15):8590-8593). Furthermore, mutations in PS1 or PS2 associated with an increase in amyloidogenic amyloid f3 peptide generation in AD are reported to be associated with a decrease in intracellular calcium level (Yoo et al. (2000) Neuron, 27(3):561-572).

Experimental traumatic brain injury has been shown to initiate massive disturbances in $Ca^{2+}$ concentrations in the brain that may contribute to further neuronal damage. Intracellular $Ca^{2+}$ may be elevated by many different ion channels. It has been further shown that channel blockers may be beneficial in the treatment of neurological motor dysfunction when administered in the acute posttraumatic period (Cheney et al. (2000) J. Neurotrauma, 17(1):83-91).

Inflammatory Diseases and Disorders

Compositions and methods provided herein may also be used in connection with treatment of inflammatory diseases. These diseases include but are not limited to asthma, chronic obstructive pulmonary disease, rheumatoid arthritis, osteoarthritis, inflammatory bowel disease, glomerulonephritis, neuroinflammatory diseases such as multiple sclerosis, and disorders of the immune system.

The activation of neutrophils (PMN) by inflammatory mediators is partly achieved by increasing cytosolic calcium concentration ($[Ca^{2+}]_i$). Certain calcium channel-mediated calcium influx in particular is thought to play an important role in PMN activation. It has been shown that trauma increases PMN store-operated calcium influx (Hauser et al. (2000) J. Trauma Injury Infection and Critical Care 48 (4): 592-598) and that prolonged elevations of $[Ca^{2+}]_i$, due to enhanced store-operated calcium influx may alter stimulus-response coupling to chemotaxins and contribute to PMN dysfunction after injury. Modulation of PMN $[Ca^{2+}]_i$ through store-operated calcium channels might therefore be useful in regulating PMN-mediated inflammation and spare cardiovascular function after injury, shock or sepsis (Hauser et al. (2001) J. Leukocyte Biology 69 (1):63-68).

Peripheral neuropathy, for example diabetic neuropathy, is a particular condition that involves both a neuronal and an inflammatory component. Without being bound by a mechanistic theory, the TRPA1 antagonists of the invention may be useful in treating peripheral neuropathies including, but not limited to, diabetic neuropathy. In addition to their use in the treatment of peripheral neuropathies (e.g., reducing inflammation), the subject inhibitors may also be useful in reducing the pain associated with peripheral neuropathy.

Neurogenic inflammation often occurs when neuronal hyperexcitability leads to the release of peptides that trigger inflammation. These peptides include substance P and CGRP. Blocking TRPA1 would reduce neuronal activity and thus could block neurogenic inflammation.

Pancreatitis is an inflammation of the pancreas. The pancreas is a large gland behind the stomach and close to the duodenum. Normally, digestive enzymes do not become active until they reach the small intestine, where they begin digesting food. But if these enzymes become active inside the pancreas, they start "digesting" the pancreas itself.

Acute pancreatitis is usually, although not exclusively, caused by gallstones or by alcohol abuse. Acute pancreatitis usually begins with pain in the upper abdomen that may last for a few days. The pain may be severe and may become constant. The pain may be isolated to the abdomen or it may reach to the back and other areas. Sometimes, and for some patients, the pain is sudden and intense. Other times, or for other patients, the pain begins as a mild pain that worsens after eating. Someone with acute pancreatitis often looks and feels very sick. Other symptoms may include swollen and tender abdomen, nausea, vomiting, fever, and rapid pulse. Severe cases of acute pancreatitis may cause dehydration and low blood pressure, and may even lead to organ failure, internal bleeding, or death.

During acute pancreatitis attacks, the blood levels of amylase and lipase are often increased by at least 3-fold. Changes may also occur in blood levels of glucose, calcium, magnesium, sodium, potassium, and bicarbonate.

The current treatment depends on the severity of the attack. Treatment, in general, is designed to support vital bodily functions, manage pain, and prevent complications. Although acute pancreatitis typically resolved in a few days, pain management during an attack is often required. The compounds disclosed herein can be used to relieve the pain associated with acute pancreatitis.

Chronic pancreatitis—If injury to the pancreas continues, chronic pancreatitis may develop. Chronic pancreatitis occurs when digestive enzymes attack and destroy the pancreas and nearby tissues, causing scarring and pain. Chronic pancreatitis may be caused by alcoholism, or by blocked, damaged, or narrowed pancreatic ducts. Additionally, hereditary factors appear to influence the disease, and in certain cases, there is no identifiable cause (so called idiopathic pancreatitis).

Most people with chronic pancreatitis have abdominal pain. The pain may get worse when eating or drinking, spread to the back, or become constant and disabling. Other symptoms include nausea, vomiting, weight loss, and fatty stools.

Relieving pain is the first step in treating chronic pancreatitis. Once the pain has been managed, a high carbohydrate and low fat dietary plan is put in place. Pancreatic enzymes may be used to help compensate for decrease enzyme production from the injured pancreas. Sometimes insulin or other drugs are needed to control blood glucose.

Although pain is typically managed using drug therapy, surgery may be necessary to relieve pain. Surgery may be necessary to drain an enlarged pancreatic duct or even to removing a portion of a seriously injured pancreas.

Pain is frequently present with chronic pancreatitis. For example, pain is present for approximately 75% of patients with alcoholic chronic pancreatitis, 50% of patients with late-onset idiopathic chronic pancreatitis, and 100% of patients with early-onset idiopathic chronic pancreatitis (DiMagno, 1999, Gastroenterology 116(5): 1252-1257).

A minority of patients with pain have readily identifiable lesions which are relatively easy to treat surgically or endoscopically. In other patients, pain is often thought to result from a variety of causes, including elevated intrapancreatic pressure, ischemia, and fibrosis. Without being bound by theory, however, these phenomena are not likely the underlying cause of the pain. Rather, pain may result from a background of neuronal sensitization induced by damage to the perineurium and subsequent exposure of the nerves to mediators and products of inflammation.

Given the importance of effective pain management in patients with chronic pancreatitis, additional therapies for treating painful symptoms are important and useful. The compounds disclosed herein can be used to manage the pain associated with chronic pancreatitis; they can be used alone or as part of an overall therapeutic treatment plan to manage patients with chronic pancreatits. For example, the compounds can be administered with pancreatic enzymes and/or insulin as part of a therapeutic regimen designed to manage patients with chronic pancreatitis.

Cancer treatments are not only painful, but they may even be toxic to healthy tissue. Some chemotherapeutic agents can cause painful neuropathy. Accordingly, the compounds disclosed herein could represent a significant possible therapeutic for the treatment of the pain and/or inflammation associated with cancer treatments that cause neuropathy.

A major function of prostaglandins is to protect the gastric mucosa. Included in this function is the modulation of intracellular calcium level in human gastric cells which plays a critical role in cell proliferation. Consequently, inhibition of prostaglandins by nonsteroidal anti-inflammatory drugs (NSAIDs) can inhibit calcium influx in gastric cells (Kokoska et al. (1998) Surgery (St Louis) 124 (2):429-437). The NSAIDs that relieve inflammation most effectively also produce the greatest gastrointestinal damage (Canadian Family Physician, January 1998, p. 101). Thus, the ability to independently modulate calcium channels in specific cell types may help to alleviate such side effect of anti-inflammatory therapy. Additionally or alternatively, administration of TRPA1 inhibitory compounds disclosed herein may be used in combination with NSAIDs, thus promoting pain relief using reduced dosage of NSAIDs.

Incontinence

Incontinence is a significant social and medical problem affecting both men and women. Incontinence has many causes including, but not limited to, age, pregnancy, radiation exposure, surgery, injury, cancer, enlargement of the prostatic, prostatic hyperplasia, and diseases of the bladder or musculature that supports the urethra. The invention contemplates methods for treating incontinence due to any of the foregoing, as well as incontinence of unknown cause or continence due to anxiety, stress, or depression.

In certain embodiments, the compounds disclosed herein are used to reduce bladder hyperactivity by decreasing the activity of the neurons that innervate the bladder. In certain embodiments, incontinence is accompanied by pain. For example, incontinence incident to bladder cystitis or incontinence incident to an injury may be accompanied by pain. When incontinence is accompanied by pain, the compound may be administered to treat both incontinence and to reduce pain.

Animal models of incontinence are often associated with an increase in the frequency of spontaneous action potentials and a chronic depolarization of the smooth muscle cells. Evidence suggests that a non-selective cation current could lead to this depolarization. Since TRPA1 mRNA is expressed in neurons that innervate bladder, blocking TRPA1 might be an effective treatment for incontinence. In addition, TRPA1 is activated by stimulation of the muscarinic type 1 acetylcholine receptor (M1, see Jordt et al. (2004) Nature 427:260-265). Antimuscarininc agents are well known drugs for the treatment of condition such as overactive bladder. Thus blocking TRPA1, a downstream target of the M1 receptor might alleviate such conditions without the side effects that are associated with muscarinic antagonists.

Temperature Regulation

Because of the effects of ion flux on arterial tension and relaxation, the subject compounds can also be used to affect thermal sensitivity. Furthermore, given that TRPA1 channels are thermal responsive channels involved in the reception and sensation of cold stimuli, TRPA1 antagonists can be used to modulate the sensation of cool, cold and decreased temperatures that often accompany pain.

Allergies

Allergies can sometimes lead to canker sores and other oral lesions. Oral lesions due to an allergy may be more likely when a person's oral tissues come into contact with the causative allergen. However, contact between the allergen and oral tissue is not necessarily required to produce an oral lesion. Exemplary allergens that can lead to oral lesions include food allergens such as fruits and vegetables (e.g., strawberries, lemons, oranges, pineapples, apples, figs, tomatoes); shellfish; chocolate; nuts; dairy (e.g., milk and cheese); cereal grains (e.g., buckwheat, wheat, oats, rye, barley, gluten protein found in grains); additives (e.g., cinnamonaldehyde (a flavoring agent), benzoic acid (a preservative); toothpastes (e.g., some people have a sensitivity to sodium laurel sulfate found in certain toothpastes and mouthwashes); nonsteroidal anti-inflammatory drugs (NSAIDs; some people have a sensitivity leading to canker sores in response to this class of drug).

The compounds disclosed herein can also be used to treat seasonal allergies, e.g., allergic rhinitis.

Combination Therapy

The subject compounds can be used alone or in combination with other pharmaceutically active agents. Examples of such other pharmaceutically active agents include, but are not limited to, anti-inflammatory agents (e.g., NSAIDS, bradykinin receptor antagonists, hormones and autacoids such as corticosteroids), anti-acne agents (e.g., retinoids), anti-wrinkle agents, anti-scarring agents, anti-incontinence agents (such as M1-receptor antagonists) anti-emetics (such as NK1 antagonists), anti-psoriatic agents, antacids, anti-proliferative agents (e.g., anti-eczema agents, anti-cancer), anti-fungal agents, anti-viral agents, anti-septic agents (e.g., antibacterials), local anaesthetics, anti-migraine agents, keratolytic agents, hair growth stimulants, hair growth inhibitors, and other agents used for the treatment of skin diseases or conditions. Certain active agents belong to more than one category.

In certain embodiments, a compound of the invention is conjointly administered with an analgesic. Suitable analgesics include, but are not limited to, opioids, glucocorticosteroids, non-steroidal anti-inflammatories, naphthylalkanones, oxicams, para-aminophenol derivatives, propionic acids, propionic acid derivatives, salicylates, fenamates, fenamate derivatives, pyrozoles, and pyrozole derivatives. Examples of such analgesic compounds include, but are not limited to, codeine, hydrocodone, hydromorphone, levorpharnol, morphine, oxycodone, oxymorphone, butorphanol, dezocine, nalbuphine, pentazocine, etodolac, indomethacin, sulindac, tolmetin, nabumetone, piroxicam, acetaminophen, fenoprofen, flurbiprofen, ibuprofen, ketoprofen, naproxen, diclofenac, oxaprozin, aspirin, diflunisal, meclofenamic acid, mefanamic acid, prednisolone, and dexamethasone. Preferred analgesics are non-steroidal anti-inflammatories and opioids (preferably morphine).

In some embodiments, the compounds disclosed herein can be admininstered in conjunction with a therapeutic whose administration causes pain. For example, a TRPA1 antagonist can be administered in conjunction with an anesthetic, to reduce the pain caused by the administration of the anaesthetic. A TRPA1 antagonist can also be administered in conjunction with a chemotherapeutic agent, to reduce the pain caused by administration of the chemotherapeutic agent.

In certain embodiments, a compound of the invention is conjointly administered with a non-steroidal anti-inflammatory. Suitable non-steroidal anti-inflammatory compounds include, but are not limited to, piroxicam, diclofenac, etodolac, indomethacin, ketoralac, oxaprozin, tolmetin, naproxen, flubiprofen, fenoprofen, ketoprofen, ibuprofen, mefenamic acid, sulindac, apazone, phenylbutazone, aspirin, celecoxib and rofecoxib.

In certain embodiments, a compound of the invention is conjointly administered with an antiviral agent. Suitable antiviral agents include, but are not limited to, amantadine, acyclovir, cidofovir, desciclovir, deoxyacyclovir, famciclovir, foscamet, ganciclovir, penciclovir, azidouridine, anasmycin, amantadine, bromovinyldeoxusidine, chlorovinyldeoxusidine, cytarbine, didanosine, deoxynojirimycin, dideoxycitidine, dideoxyinosine, dideoxynucleoside, edoxuidine, enviroxime, fiacitabine, foscamet, fialuridine, fluorothymidine, floxuridine, hypericin, interferon, interleukin, isethionate, nevirapine, pentamidine, ribavirin, rimantadine, stavirdine, sargramostin, suramin, trichosanthin, tribromothymidine, trichlorothymidine, vidarabine, zidoviridine, zalcitabine 3-azido-3-deoxythymidine, 2',3'-dideoxyadenosine (ddA), 2',3'-dideoxyguanosine (ddG), 2',3'-dideoxycytidine (ddC), 2',3'-dideoxythymidine (ddT), 2'3'-dideoxy-dideoxythymidine (d4T), 2'-deoxy-3'-thia-cytosine (3TC or lamivudime), 2',3'-dideoxy-2'-fluoroadenosine, 2',3'-dideoxy-2'-fluoroinosine, 2',3'-dideoxy-2'-fluorothymidine, 2',3'-dideoxy-2'-fluorocytosine, 2'3'-dideoxy-2',3'-didehydro-2'-fluorothymidine (Fd4T), 2'3'-dideoxy-2'-beta-fluoroadenosine (F-ddA), 2'3'-dideoxy-2'-beta-fluoro-inosine (F-ddI), and 2',3'-dideoxy-2'-beta-fluorocytosine (F-ddC), trisodium phosphomonoformate, trifluorothymidine, 3' azido-3' thymidine (AZT), dideoxyinosine (ddI), and idoxuridine.

In certain embodiments, a compound of the invention is conjointly administered with an antibacterial agent. Suitable antibacterial agents include, but are not limited to, amanfadine hydrochloride, amanfadine sulfate, amikacin, amikacin sulfate, amoglycosides, amoxicillin, ampicillin, amsamycins, bacitracin, beta-lactams, candicidin, capreomycin, carbenicillin, cephalexin, cephaloridine, cephalothin, cefazolin, cephapirin, cephradine, cephaloglycin, chilomphenicols, chlorhexidine, chloshexidine gluconate, chlorhexidine hydrochloride, chloroxine, chlorquiraldol, chlortetracycline, chlortetracycline hydrochloride, ciprofloxacin, circulin, clindamycin, clindamycin hydrochloride, clotrimazole, cloxacillin, demeclocycline, diclosxacillin, diiodohydroxyquin, doxycycline, ethambutol, ethambutol hydrochloride, erythromycin, erythromycin estolate, erhmycin stearate, farnesol, floxacillin, gentamicin, gentamicin sulfate, gramicidin, giseofulvin, haloprogin, haloquinol, hexachlorophene, iminocylcline, iodochlorhydroxyquin, kanamycin, kanamycin sulfate, lincomycin, lineomycin, lineomycin hydrochloride, macrolides, meclocycline, methacyline, methacycline hydrochloride, methenine, methenamine hippurate, methenamine mandelate, methicillin, metonidazole, miconazole, miconazole hydrochloride, minocycline, minocycline hydrochloride, mupirocin, nafcillin, neomycin, neomycin sulfate, netimicin, netilmicin sulfate, nitrofurazone, norfloxacin, nystatin, octopirox, oleandomycin, orcephalosporins, oxacillin, oxyteacline, oxytetracycline hydrochloride, parachlorometa xylenol, paromomycin, paromomycin sulfate, penicillins, penicillin G, penicillin V, pentamidine, pentamidine hydrochloride, phenethicillin, polymyxins, quinolones, streptomycin sulfate, tetracycline, tobramycin, tolnaftate, triclosan, trifampin, rifamycin, rolitetracycline, spectinomycin, spiramycin, struptomycin, sulfonamide, tetracyclines, tetracycline, tobramycin, tobramycin sulfate, triclocarban, triclosan, trimethoprim-sulfamethoxazole, tylosin, vancomycin, and yrothricin.

Examples of retinoids that be administered with the subject compounds, e.g., where the TRPA1 inhibitor can be used to reduce the pain and/or inflammatory effect of the retinoid, include, but are not limited to, compounds such as retinoic acid (both cis and trans), retinol, adapalene, vitamin A and tazarotene. Retinoids are useful in treating acne, psoriasis, rosacea, wrinkles and skin cancers and cancer precursors such as melanoma and actinic keratosis.

Similarly, the subject compounds can be used in conjunction with keratolytic agents include benzoyl peroxide, alpha hydroxyacids, fruit acids, glycolic acid, salicylic acid, azelaic acid, trichloroacetic acid, lactic acid and piroctone.

The subject compounds can be used with anti-acne agents, anti-eczema agents and anti-psoratic agents. Compounds particlarly useful in treating acne include azelaic acid (an aliphatic diacid with antiacne properties), anthralin (a diphenolic compound with antifungal and antipsoriatic properties), and masoprocol (nordihydroguaiaretic acid, a tetraphenolic compound with antioxidant properties, also useful in the treatment of actinic keratosis) and analogs thereof (such as austrobailignan 6, oxoaustrobailignan 6,4'-O-methyl-7,7'-dioxoaustrobailignan 6, macelignan, demethyldihydroguaiaretic acid, 3,3',4-trihydroxy-4'-methoxylignan, Saururenin, 4-hydroxy-3,3',4'-trimethoxylignan, and isoanwulignan). Anti-eczema agents include pimecrolimus and tacrolimus. Anti-psoriatic active agents suitable for use in the present invention include retinoids (including isomers and derivatives of retinoic acid, as well as other compounds that bind to the retinoic acid receptor, such as retinoic acid, acitretin, 13-cis-retinoic acid (isotretinoin), 9-cis-retinoic acid, tocopheryl-retinoate (tocopherol ester of retinoic acid (trans- or cis-)), etretinate, motretinide, 1-(13-cis-retinoyloxy)-2-propanone, 1-(13-cis-retinoyloxy)-3-decanoyloxy-2-propanone, 1,3-bis-(13-cis-retinoyloxy)-2-propanone, 2-(13-cis-retinoyloxy)-acetophenone, 13-cis-retinoyloxymethyl-2,2-dimethyl propanoate, 2-(13-cis-retinoyloxy)-n-methylacetamide, 1-(13-cis-retinoyloxy)-3-hydroxy-2-propanone, 1-(13-cis-retinoyloxy)-2,3-dioleoylpropanone, succinimidyl 13-cis-retinoate, adapalene, and tazarotene), salicylic acid (monoammonium salt), anthralin, 6-azauridine, vitamin D derivatives (including but not limited to Rocaltrol (Roche Laboratories), EB 1089 (24α,26α,27α-trihomo-22,24-diene-1α,25-(OH)$_2$-D$_3$), KH 1060 (20-epi-22-oxa-24α,26α,27α-trihomo-1α,25-(OH)$_2$-D$_3$), MC 1288, GS 1558, CB 1093, 1,25-(OH)$_2$-16-ene-D$_3$, 1,25-(OH)$_2$-16-ene-23-yne-D$_3$, and 25-(OH)$_2$-16-ene-23-yne-D$_3$, 22-oxacalcitriol; 1α-(OH)D$_5$ (University of Illinois), ZK 161422 and ZK 157202 (Institute of Medical Chemistry-Schering AG), alfacalcidol, calcifediol, calcipotriol (calcipotriene), maxacalcitriol, colecalciferol, doxercalciferol, ergocalciferol, falecalcitriol, lexacalcitol, maxacalcitol, paricalcitol, secalciferol, seocalcitol, tacalcitol, calcipotriene, calcitriol, and other analogs as disclosed in U.S. Pat. No. 5,994,332), pyrogallol, and tacalcitol.

The compounds disclosed herein can also be administered with vitamins and derivatives thereof including Vitamin A, ascorbic acid (Vitamin C), alpha-tocopherol (Vitamin E), 7-dehydrocholesterol (Vitamin D), Vitamin K, alpha-lipoic acid, lipid soluble anti-oxidants, and the like. They can also be used with skin protectants, such allantoin and esculin.

In addition to TRPA1, other TRP channels have been implicated in pain reception and/or sensation. For example, certain TRPM channels including TRPM8 have been implicated in the reception and/or sensation of pain. Accordingly, in certain embodiments, the methods of the present invention include treating pain by administering (i) a combination of a selective TRPA1 antagonist and a selective TRPM8 antagonist; (ii) a combination of a selective TRPA1 antagonist, a selective TRPM8 antagonist, and one or more of a selective TRPV1 and/or TRPV3 antagonist; (iii) a cross-TRP inhibitor that antagonizes a function of TRPA1 and TRPM8; or (iv) a pan inhibitor that antagonizes a function of TRPA1, TRPM8, and one or more of TRPV1 and TRPV3.

In certain embodiments, a compound of the invention is conjointly administered with one or more additional compounds that antagonize the function of a different channel. By way of example, a compound of the invention may be conjointly administered with one or more compounds that antagonize TRPV1, TRPM8, and/or TRPV3. The compound(s) that antagonize TRPV1, TPRM8, or TRPV3 may be selective for TRPV1, TRPM8 or TRPV3 (e.g., inhibit TRPV1 or TRPV3 10, 100, or 1000 fold more strongly than TRPA1). Alternatively, the compound(s) that antagonize TRPV1 or TRPV3 may cross react with other TRP channels.

Pharmaceutical Compositions

While it is possible for a compound disclosed herein to be administered alone, it is preferable to administer the compound as a pharmaceutical formulation, where the compound is combined with one or more pharmaceutically acceptable excipients or carriers. The compounds disclosed herein may be formulated for administration in any convenient way for use in human or veterinary medicine. In certain embodiments, the compound included in the pharmaceutical preparation may be active itself, or may be a prodrug, e.g., capable of being converted to an active compound in a physiological setting.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Examples of pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21) cyclodextrins such as anionically charged sulfobutyl ether β-cyclodextrins or hydroxypropyl-beta-cyclodextrins; and (22) other non-toxic compatible substances employed in pharmaceutical formulations.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Solid dosage forms (e.g., capsules, tablets, pills, dragees, powders, granules and the like) can include one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents.

Liquid dosage forms can include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

The tablets, and other solid dosage forms of the pharmaceutical compositions disclosed herein, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The formulations disclosed herein can be delivered via a device. Exemplary devices include, but are not limited to, a catheter, wire, stent, or other intraluminal device. Further exemplary delivery devices also include a patch, bandage, mouthguard, or dental apparatus. Transdermal patches have the added advantage of providing controlled delivery of a compound disclosed herein to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, drops, solutions and the like, are also contemplated as being within the scope of this invention.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled.

Examples of other biodegradable polymers include poly (orthoesters) and poly(anhydrides). Depot injectable formulations are also prepared by entrapping the drug in liposomes or microemulsions that are compatible with body tissue.

When the compounds disclosed herein are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The formulations can be administered topically, orally, transdermally, rectally, vaginally, parentally, intranasally, intrapulmonary, intraocularly, intravenously, intramuscularly, intraarterially, intrathecally, intracapsularly, intraorbitally, intracardiacly, intradermally, intraperitoneally, transtracheally, subcutaneously, subcuticularly, intraarticularly, subcapsularly, subarachnoidly, intraspinally, intrasternally or by inhalation.

One specific embodiment is an antitussive composition for peroral administration comprising an agent that inhibits both a TRPA1-mediated current with an $IC_{50}$ of 1 micromolar or less, and an orally-acceptable pharmaceutical carrier in the form of an aqueous-based liquid, or solid dissolvable in the mouth, selected from the group consisting of syrup, elixer, suspension, spray, lozenge, chewable lozenge, powder, and chewable tablet. Such antitussive compositions can include one or more additional agents for treating cough, allergy or asthma symptom selected from the group consisting of: antihistamines, 5-lipoxygenase inhibitors, leukotriene inhibitors, H3 inhibitors, β-adrenergic receptor agonists, xanthine derivatives, α-adrenergic receptor agonists, mast cell stabilizers, expectorants, NK1, NK2 and NK3 tachykinin receptor antagonists, and $GABA_B$ agonists.

Still another embodiment is a metered dose aerosol dispenser containing an aerosol pharmaceutical composition for pulmonary or nasal delivery comprising an agent that inhibits a TRPA1-mediated current with an $IC_{50}$ of 1 micromolar or less. For instance, it can be a metered dose inhaler, a dry powder inhaler or an air-jet nebulizer.

Dosages

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound disclosed herein employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, intravenous, intracerebroventricular and subcutaneous doses of the compounds of this invention for a patient will range from about 0.0001 to about 100 mg per kilogram of body weight per day. For example, the dose can be 1-50, 1-25, or 5-10 mg/kg.

If desired, the effective daily dose of the active compound may be administered as two, three, four, five, six or more sub-doses administered separately at appropriate intervals throughout the day, optionally, in unit dosage forms.

Disease and Injury Models

Compounds that antagonize TRPA1 function may be useful in the prophylaxis and treatment of any of the foregoing injuries, diseases, disorders, or conditions. In addition to in vitro assays of the activity of these compounds, their efficacy can be readily tested in one or more animal models. There are numerous animal models for studying pain. The various models use various agents or procedures to simulate pain resulting from injuries, diseases, or other conditions. Blackburn-Munro (2004) Trends in Pharmacological Sciences 25: 299-305 (see, for example, Tables 1, 3, or 4). Behavioral characteristics of challenged animals can then be observed. Compounds or procedures that may reduce pain in the animals can be readily tested by observing behavioral characteristics of challenged animals in the presence versus the absence of the test compound(s) or procedure.

Exemplary behavioral tests used to study chronic pain include tests of spontaneous pain, allodynia, and hyperalgesia. Id. To assess spontaneous pain, posture, gait, nocifensive signs (e.g., paw licking, excessive grooming, excessive exploratory behavior, guarding of the injured body part, and self-mutilation) can be observed. To measure evoked pain, behavioral responses can be examined following exposure to heat (e.g., thermal injury model).

Exemplary animal models of pain include, but are not limited to, the Chung model, the carageenan induced hyperalgesia model, the Freund's complete adjuvant induced hyperalgesia model, the thermal injury model, the formalin model and the Bennett Model. The Chung model of neuropathic pain (without inflammation) involves ligating one or more spinal nerves. Chung et al. (2004) Methods Mol Med 99: 35-45; Kim and Chung (1992) Pain 50: 355-363. Ligation of the spinal nerves results in a variety of behavioral changes in the animals including heat hyperalgesia, cold allodynia, and ongoing pain. Compounds that antagonize TRPA1 can be administered to ligated animals to assess whether they diminish these ligation-induced behavioral changes in comparison to that observed in the absence of compound.

Carageenan induced hyperalgesia and Freund's complete adjuvant (FCA) induced hyperalgesia are models of inflammatory pain. Walker et al. (2003) Journal of Pharmacol Exp Ther 304: 56-62; McGaraughty et al. (2003) Br J Pharmacol 140: 1381-1388; Honore et al. (2005) J Pharmacol Exp Ther. Compounds that antagonize TRPA1 can be administered to carrageenan or FCA challenged animals to assess whether they diminish thermal hyperalgesia in comparison to that observed in the absence of compound. In addition, the ability of compounds that antagonize TRPA1 function to diminish cold and/or mechanical hypersensitivity can also be assessed in these models. Typically, the carrageenan induced hyperalgesia model is believed to mimic acute inflammatory pain and the CFA model is believed to mimic chronic pain and chronic inflammatory pain.

Exemplary models of inflammatory pain include the rat model of intraplantar bradykinin injection. Briefly, the baseline thermal sensitivity of the animals is assessed on a Hargreave's apparatus. TRPA1 blockers are then administered systemically. Bradykinin is subsequently injected into the paw and a hyperalgesia is allowed to develop. Thermal escape latency is then measured at multiple time points over the next few hours (Chuang et al., 2001; Vale et al., 2004).

Inflammation is often an important contributing factor to pain. As such, it is useful to identify compounds that act as anti-inflammatories. Many compounds that reduce neural activity also prevent neurogenic inflammation. To measure inflammation directly, the volume of a rat paw can be assessed using a plethysmometer. After baseline measurement is taken, carrageenan can be injected into the paw and the volume can be monitored over the course of hours in animals that have been treated with vehicle or drug. Drugs that reduce the paw swelling are considered to be anti-inflammatory.

Migraines are associated with significant pain and inability to complete normal tasks. Several models of migraine exist including the rat neurogenic inflammation model, (see Buzzi et al (1990) Br J Pharmacol; 99:202-206), and the Burstein Model (see Strassman et al., (1996) Nature 384: 560-564).

The Bennett model uses prolonged ischemia of the paw to mirror chronic pain. Xanthos et al. (2004) J Pain 5: S1. This provides an animal model for chronic pain including post-operative pain, complex regional pain syndrome, and reflex sympathetic dystrophy. Prolonged ischemia induces behavioral changes in the animals including hyperalgesia to mechanical stimuli, sensitivity to cold, pain behaviors (e.g., paw shaking, licking, and/or favoring), and hyperpathia. Compounds that antagonize TRPA1 can be administered to challenged animals to assess whether they diminish any or all of these behaviors in comparison to that observed in the absence of compound. Similar experiments can be conducted in a thermal injury or UV-burn model which can be used to mimic post-operative pain.

Additional models of neuropathic pain include central pain models based on spinal cord injury. Chronic pain is generated by inducing a spinal cord injury, for example, by dropping a weight on a surgically exposed area of spinal cord (e.g., weight-drop model). Spinal cord injury can additionally be induced by crushing or compressing the spinal cord, by delivering neurotoxin, using photochemicals, or by hemisecting the spinal cord. Wang and Wang (2003).

Additional models of neuropathic pain include peripheral nerve injury models. Exemplary models include, but are not limited to, the neuroma model, the Bennett model, the Seltzer model, the Chung model (ligation at either L5 or L5/L6), the sciatic cryoneurolysis model, the inferior caudal trunk resection model, and the sciatic inflammatory neuritis model. Id.

Exemplary models of neuropathic pain associated with particular diseases are also available. Diabetes and shingles are two diseases often accompanied by neuropathic pain. Even following an acute shingles episodes, some patients continue to suffer from postherpetic neuralgia and experience persistent pain lasting years. Neuropathic pain caused by shingles and/or postherpetic neuralgia can be studied in the postherpetic neuralgia model (PHN). Diabetic neuropathy can be studied in diabetic mouse models, as well as chemically induced models of diabetic neuropathy. Wang and Wang (2003).

As outlined above, cancer pain may have any of a number of causes, and numerous animal models exist to examine cancer pain related to, for example, chemotherapeutics or tumor infiltration. Exemplary models of toxin-related cancer pain include the vincristine-induced peripheral neuropathy model, the taxol-induced peripheral neuropathy model, and the cisplatin-induced peripheral neuropathy model. Wang and Wang (2003). An exemplary model of cancer pain caused by tumor infiltration is the cancer invasion pain model (CIP). Id.

Primary and metastatic bone cancers are associated with tremendous pain. Several models of bone cancer pain exist including the mouse femur bone cancer pain model (FBC), the mouse calcaneus bone cancer pain model (CBC), and the rat tibia bone cancer model (TBC). Id.

An additional model of pain is the formalin model. Like the carrageenan and CFA models, the formalin model involves injection of an irritant intradermally or intraperitoneally into an animal. Injection of formalin, a 37 percent solution of formaldehyde, is the most commonly used agent for intradermal paw injection (the formalin test). Injection of a 0.5 to 15 percent solution of formalin (usually about 3.5%) into the dorsal or plantar surface of the fore- or hindpaw produces a biphasic painful response of increasing and decreasing intensity for about 60 minutes after the injection. Typical responses include the paw being lifted, licked, nibbled, or shaken. These responses are considered nociceptive. The initial phase of the response (also known as the Early Phase), which lasts 3 to 5 minutes, is probably due to direct chemical stimulation of nociceptors. This is followed by 10 to 15 minutes during which animals display little behavior suggestive of nociception. The second phase of this response (also known as the Late Phase) starts about 15 to 20 minutes after the formalin injection and lasts 20 to 40 minutes, initially rising with both number and frequency of nociceptive behaviors, reaching a peak, then falling off. The intensities of these nociceptive behaviors are dependent on the concentration of formalin used. The second phase involves a period of sensitization during which inflammatory phenomena occur. The two phases of responsiveness to formalin injection makes the formalin model an appropriate model for studying mociceptive and acute inflammatory pain. It may also model, in some respects, neuropathic pain.

In addition to any of the foregoing models of chronic pain, compounds that antagonize TRPA1 function can be tested in one or more models of acute pain. Valenzano et al. (2005) Neuropharmacology 48: 658-672. Regardless of whether compounds are tested in models of chronic pain, acute pain, or both, these studies are typically (though not exclusively) conducted, for example, in mice, rats, or guinea pigs. Additionally, compounds can be tested in various cell lines that provide in vitro assays of pain. Wang and Wang (2003).

Many individuals seeking treatment for pain suffer from visceral pain. Animal models of visceral pain include the rat model of inflammatory uterine pain (Wesselmann et al., (1997) Pain 73:309-317), injection of mustard oil into the gastrointestinal tract to mimic irritable bowel syndrome (Kimball et al., (2005) Am J Physiol Gastrointest Liver Physiol, 288(6):G1266-73), injection of mustard oil into the bladder to mimic overactive bladder or bladder cystitis (Riazimand (2004), BJU 94: 158-163). The effectiveness of a TRPA1 compound can be assessed by a decrease in writhing, gastrointestinal inflammation or bladder excitability.

For testing the efficacy of TRPA1 antagonists for the treatment of cough, experiments using the conscious guinea pig model of cough can be readily conducted. Tanaka and Maruyama (2003) Journal Pharmacol Sci 93: 465-470; McLeod et al. (2001) Br J Pharmacol 132: 1175-1178. Briefly, guinea pigs serve as a useful animal model for cough because, unlike other rodents such as mice and rats, guinea pigs actually cough. Furthermore, guinea pig coughing appears to mimic human coughing in terms of the posture, behavior, and appearance of the coughing animal.

To induce cough, conscious guinea pigs are exposed to an inducing agent such as citric acid or capsaicin. The response of the animal is measured by counting the number of coughs. The effectiveness of a cough suppressing agent, for example a compound that inhibits TRPA1, can be measured by administering the agent and assessing the ability of the agent to decrease the number of coughs elicited by exposure to citric acid, capsaicin, or other similar cough-inducing agent. In this way, TRPA1 inhibitors for use in the treatment of cough can be readily evaluated and identified.

Additional models of cough include the unconscious guinea pig model. Rouget et al. (2004) Br J Pharmacol 141: 1077-1083. Either of the foregoing models can be adapted for use with other animals capable of coughing. Exemplary additional animals capable of coughing include cats and dogs.

Numerous rodent models of incontinence exist. These include models of incontinence induced by nerve damage, urethral impingement and inflammation. Models of urethral impingement include the rat bladder outflow obstruction model. (Pandita, R K, and Andersson K E. Effects of intravesical administration of the $K^+$ channel opener, Z.D6169, in conscious rats with and without bladder outflow obstruction. J Urol 162: 943-948, 1999). Inflammatory models include injection of mustard oil into the bladder.

To test the effectiveness of a TRPA1 inhibitor compound in treating incontinence, varying concentrations of compound (e.g., low, medium, and high concentration) can be administered to rats following surgical partial bladder outlet obstruction (BOO). Efficacy of the varying doses of TRPA1 inhibitory compound can be compared to controls administered excipients alone (sham control). Efficacy can further be compared to rats administered a positive control, such as atropine. Atropine is expected to decrease bladder over-activity following partial bladder outlet obstruction in the BOO model. Note that when testing compounds in the BOO model, compounds can be administered directly to the bladder or urethra (e.g., by catheter) or compounds can be administered systemically (e.g., orally, intraveneously, intraperitoneally, etc).

Several rat models of pancreatitic pain have recently been described (Lu, 2003, Anesthesiology 98(3): 734-740; Winston et al., 2003, Journal of Pain 4(6): 329-337). Lu et al. induced pancreatitis by systemic delivery of dibutylin dichloride in rats. Rats showed an increase in withdrawal events after von Frey filament stimulation of the abdomen and decreased withdrawal latency after thermal stimulation during a period of 7 days. The pain state induced in these animals was also characterized by increased levels of substance P in spinal cords (Lu, et al., 2003). To test the efficacy of a TRPA1 inhibitor in this model, a TRPA1 inhibitor can be administered following or concurrently with delivery of dibutylin dichloride. Control animals can be administered a carrier or a known pain reliever. Indicia of pain can be measured. Efficacy of a TRPA1 inhibitor can be evaluated by comparing the indicia of pain observed in animals receiving a TRPA1 inhibitor to that of animals that did not receive a TRPA1 inhibitor. Additionally, efficacy of a TRPA1 inhibitor can be compared to that of known pain medicaments.

The efficacy of von Frey filament testing as a means to measure nociceptive behavior was also shown by inducing pancreatitis by systemic L-arginine administration (Winston et al, 2003). The efficacy of a TRPA1 inhibitor can similarly be tested following pancreatitis induced by systemic L-arginine administration.

Lu et al. also described direct behavioral assays for pancreatic pain using acute noxious stimulation of the pancreas via an indwelling ductal canula in awake and freely moving rats. These assays included cage crossing, rearing, and hind limb extension in response to intrapancreatic bradykinin infusion. Intrathecal administration of either D-APV (NMDA receptor antagonist) or morphine alone partially reduced visceral pain behaviors in this model. Combinations of both reduced pain behaviors to baseline. The efficacy of a TRPA1 inhibitor can similarly be tested in this system.

Any of the foregoing animal models may be used to evaluate the efficacy of a TRPA1 inhibitor in treating pain associated with pancreatitis. The efficacy can be compared to a no treatment or placebo control. Additionally or alternatively, efficacy can be evaluated in comparison to one or more known pain relieving medicaments.

The following examples are meant to be illustrative and are not meant to be limiting in any way.

EXAMPLES

Example 1

Synthesis of Exemplary Compounds

The compounds disclosed herein can be prepared using the scheme outlined below.

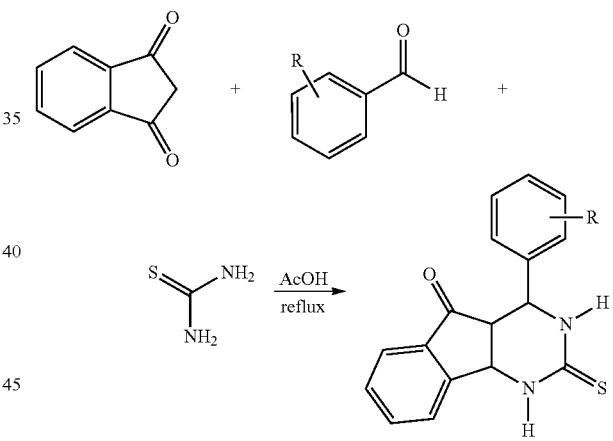

Example 2

Synthesis of Additional Exemplary Compounds

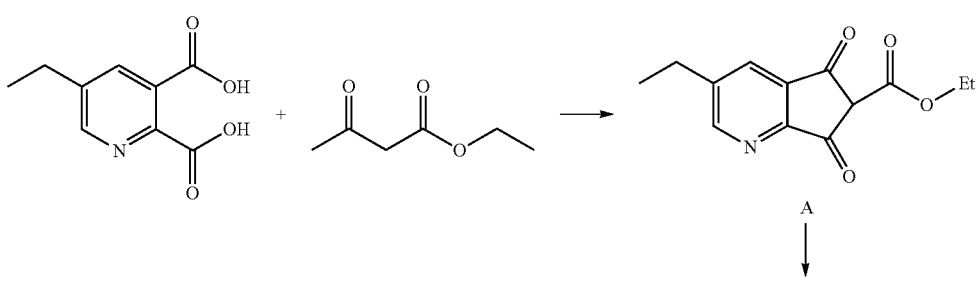

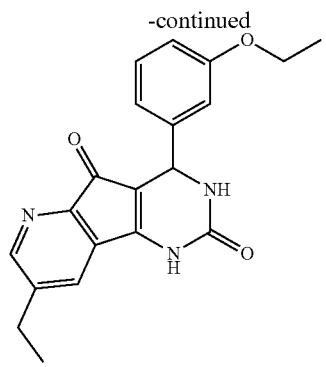

B

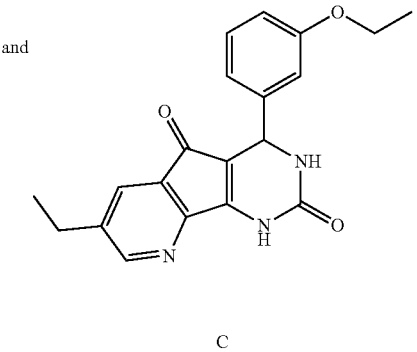

and

C

Ethyl 3-ethyl-5,7-dioxo-6,7-dihydro-5H-cyclopenta[b]pyridine-6-carboxylate (Compound A)

The mixture of 5-ethylpyridine-2,3-dicarboxylic acid (1.620 g, 8.3 mmol) in anhydrous $Ac_2O$ (4.7 mL) was mixed and cooled to 0° C. To this mixture at 0° C. was slowly added was slowly added ethyl 3-oxobutanoate (1.05 mL, 8.3 mmol) and anhydrous $Et_3N$ (2.3 mL, 16.6 mol) and then the reaction was allowed to stir at room temperature for 3 days. The reaction was diluted with HCl aqueous solution (90 mL, 0.27 M). The aqueous phase was washed with ethyl acetate twice. Golden needle crystal was crystallized out from aqueous phase to give the target compound (949 mg, 46%).

Compound B and C:

Ethyl 3-ethyl-5,7-dioxo-6,7-dihydro-5H-cyclopenta[b]pyridine-6-carboxylate (600 mg, 2.4 mmol), 3-ethoxybenzaldehyde (364 mg, 2.4 mmol) and urea (288 mg, 4.8 mmol) was added to acetic acid (2.5 mL) and the reaction was heated at 90° C. for 4 hours. The reaction was concentrated in high vacuo. The residue was purified by column chromatography (MeOH: DCM=1:100 to 1:25) to give the target compound B (20 mg) and compound C (14.4 mg) as yellow solids. The structures were determined by $^1H$-$^{13}C$ HMBC NMR

Example 2

Patch Clamp Experiments

Patch clamp experiments permit the detection of currents through the TRPA1 channel in the cell line described above. The whole-cell configuration of the patch clamp technique was used to test the compounds described herein. In normal whole-cell patch clamp recordings, a glass electrode is brought into contact with a single cell and a high-resistance (gigaohm) seal is established with the cell membrane. The membrane is then ruptured to achieve the whole-cell configuration, permitting control of the voltage of the cell membrane and measurement of currents flowing across the membrane using the amplifier attached to the electrode and resulting in the replacement of cytoplasm with the pipette solution.

TRPA1 cells were induced 20-48 hours, removed from growth plates, and replated at low density (to attain good single-cell physical separation) on glass coverslips for measurement. In some cases, cells were grown in low density overnight on glass coverslips. Potential blockers were tested for ability to block current in the continued presence of AITC.

Example 3

Testing of TRPA1 Antagonists in a Thermal Injury Model of Pain

The thermal injury model can be used to evaluate the effectiveness of an exemplary TRPA1 inhibitor in the treatment of nociceptive pain using the following protocol. Male Holtzman rats (approximately 300 grams) may be tested on thermal escape using a Hargreaves type apparatus. Under light anesthesia, a thermal injury (52° C. for 45 seconds) can be applied to one heel. The animals can be tested for thermal escape latency of the injured and uninjured paw before and at 30, 60, 80, and 120 minutes after injury. Drug (a TRPA1 inhibitor) or vehicle (0.5% methylcellulose) can be administered after the baseline measurement and approximately 15-20 minutes prior to the thermal injury. In addition to the escape latency measurement, behavioral observations can be made throughout the experiment.

Example 4

Testing of TRPA1 Antagonists in the Chung Model of Neuropathic Pain

Briefly, male Sprague Dawley rats (approximately 175 grams) can be prepared with ligation of the L4/5 nerve roots. After 5-8 days, the animals can be tested for tactile allodynia using Von Frey hairs. Thresholds can be assessed with the "up-down" method. Drug or vehicle can be administered and the animals can be tested periodically.

INCORPORATION BY REFERENCE

All publications and patents mentioned herein are hereby incorporated by reference in their entirety as if each individual publication or patent was specifically and individually indicated to be incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A compound having Formula VIII, or a pharmaceutically acceptable salt thereof:

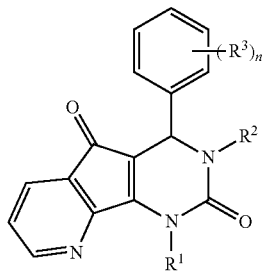

Formula VIII wherein each of $R^1$ and $R^2$ is, independently, H, optionally substituted $C_{1-6}$ alkyl, arylalkyl, heteroarylalkyl, alkoxyalkyl, $COR^{10}$, $CO_2R^{10}$, $CH_2CO_2R^{10}$, or $CONHR^{10}$, where $R^{10}$ is H or optionally substituted $C_{1-6}$ alkyl; each $R_3$ is, independently, hydroxyl, optionally substituted $C_{1-6}$ alkoxy, optionally substituted $C_{1-6}$ alkenyloxy, alkyloxyalkoxy, cyano, acyl, amino, optionally substituted alkylamino, aminoalkyl, amido, acylamino, alkylurea, alkylcarbamoyl, carboxyl, optionally substituted alkylcarboxyl, thioyl, optionally substituted alkylthio, $SO_3H$, optionally substituted alkylsulfinyl, or optionally substituted alkylsulfonyl; and n is 1-3.

2. The compound of claim 1, wherein n is 1.
3. The compound of claim 1, wherein $R^3$ is alkoxy.
4. The compound of claim 1, wherein $R^3$ is alkenyloxy.
5. The compound of claim 1, wherein each of $R^1$ and $R^2$ is, independently, H or optionally substituted $C_{1-6}$ alkyl.
6. The compound of claim 1, wherein the compound has the Formula IX.

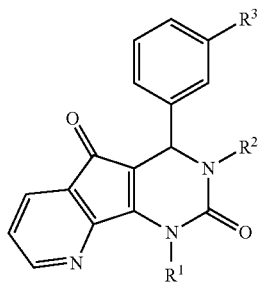

Formula IX

7. The compound of claim 1, wherein the compound has the Formula IXa.

Formula IXa

8. A pharmaceutical composition comprising a pharmaceutically-acceptable carrier and a compound having Formula VIII, or a pharmaceutically acceptable salt thereof:

Formula VIII wherein each of $R^1$ and $R^2$ is, independently, H, optionally substituted $C_{1-6}$ alkyl, arylalkyl, heteroarylalkyl, alkoxyalkyl, $COR^{10}$, $CO_2R^{10}$, $CH_2CO_2R^{10}$, or $CONHR^{10}$, where $R^{10}$ is H or optionally substituted $C_{1-6}$ alkyl; each $R^3$ is, independently, hydroxyl, optionally substituted $C_{1-6}$ alkoxy, optionally substituted $C_{1-6}$ alkenyloxy, alkyloxyalkoxy, cyano, acyl, amino, optionally substituted alkylamino, aminoalkyl, amido, acylamino, alkylurea, alkylcarbamoyl, carboxyl, optionally substituted alkylcarboxyl, thioyl, optionally substituted alkylthio, $SO_3H$, optionally substituted alkylsulfinyl, or optionally substituted alkylsulfonyl; and n is 1-3.

9. The composition of claim 8, wherein n is 1.
10. The composition of claim 8, wherein $R^3$ is alkoxy.
11. The composition of claim 8, wherein $R^3$ is alkenyloxy.

* * * * *